United States Patent
Zofchak et al.

(10) Patent No.: US 6,613,866 B2
(45) Date of Patent: Sep. 2, 2003

(54) URETHANE SURFACTANTS AND THEIR USE IN PERSONAL CARE FORMULATIONS

(75) Inventors: Albert Zofchak, Matawan, NJ (US); Madeline Kenney, Caldwell, NJ (US); John Obeji, Clifton, NJ (US); Michael Mosquera, Forked River, NJ (US)

(73) Assignee: Alzo International Inc., Sayreville, NJ (US)

( * ) Notice: Subject to any disclaimer, the term of this patent is extended or adjusted under 35 U.S.C. 154(b) by 0 days.

(21) Appl. No.: 09/892,103

(22) Filed: Jun. 26, 2001

(65) Prior Publication Data

US 2002/0015688 A1 Feb. 7, 2002

Related U.S. Application Data

(62) Division of application No. 09/275,303, filed on Mar. 24, 1999, now Pat. No. 6,315,991.

(51) Int. Cl.[7] .............................................. C08G 18/28
(52) U.S. Cl. .............................. 528/71; 528/49; 560/25; 560/115; 560/129; 560/158; 525/453; 525/454; 525/460
(58) Field of Search ..................... 528/49, 71; 560/158, 560/115, 129, 25; 525/453, 454, 460

(56) References Cited

U.S. PATENT DOCUMENTS 6,140,412 A * 10/2000 Saitoh et al.
6,258,348 B1 * 7/2001 Tsivkin

FOREIGN PATENT DOCUMENTS

WO  9946130  * 9/1999

\* cited by examiner

*Primary Examiner*—Rachel Gorr
(74) *Attorney, Agent, or Firm*—Henry D. Coleman; Coleman Sudol Sapone, P.C.

(57) ABSTRACT

The present invention is directed to monomeric and polymeric compositions based upon polymeric urethane surfactants which are derived from linear, branched, or aromatic compounds of synthetic or natural origin, preferably from tertiary amines and diisocyanate compounds. The urethane polymers of the present invention may be in the form of betaines, quaternium salts, tertiary amine salts or N-oxides. The compounds of the present invention may be incorporated into personal care formulations such as cosmetics, dental care products and toiletries to improve at least one and preferably two or more characteristics of such formulations.

10 Claims, No Drawings

URETHANE SURFACTANTS AND THEIR USE IN PERSONAL CARE FORMULATIONS

This application is a division of application Ser. No. 09/275,303, filed Mar. 24, 1999, now U.S. Pat. No. 6,315,991.

FIELD OF THE INVENTION

The present invention is directed to monomeric and polymeric compositions based upon urethane surfactants which are generally derived from linear, branched, or aromatic compounds of synthetic or natural origin, preferably from tertiary amines and diisocyanate compounds. The urethane betaines of the present invention may be incorporated into personal care formulations such as cosmetics, dental care products and toiletries to improve or modify at least two of the characteristics of such formulations.

BACKGROUND OF THE INVENTION

Surfactants, such as Betaines, amine oxides and quaternaries (from $C_6$–$C_{22}$) have been used on a commercial basis in the cosmetic, toiletry and personal care industry for the past 40 years primarily as surfactants for their mildness and lack of irritation on a commercial basis. The aforementioned surfactants have been prepared from natural oils, such as coconut oil, palm kernal oil, soybean oil, safflower seed oil, corn oil, etc. The oils are reacted with amine derivatives such as dimethylaminopropylamine, diethylaminopropyl amine, etc. via transamidation with caustic catalysts to yield the linear $C_6$ through $C_{22}$ dimethylaminopropyl amine derivatives. Similarly, linear fatty acids ranging from $C_6$ through $C_{22}$ have been reacted to form the linear tertiary amine salts which upon application of heat drove off water to form the corresponding $C_6$ through $C_{22}$ linear dimethylaminopropylamine derivative. Aromatic acids such as benzoic acid as well as branched acids similarly have been reacted to form the resultant aromatic dimethylamidopropyl amine or iso-dimethylamido propylamine which could serve as a building block for the betaine. However, aromatic backboned surfactants have not found wide commercial use.

Over the years, betaines, amine oxides and quaternaries have become commodity products used in a wide array of applications ranging from shampoos, nonirritating baby shampoos, liquid soaps, dish detergents (to preclude introduction of phosphate builders), body scrubs, shaving creams, etc. When the pH of a cosmetic or toiletry product incorporating betaines is dropped to a pH slightly below about 7.0, the betaine becomes mildly cationic and improved feel and combability of hair results. When coupled with amine oxides, the combination yields a high degree of hair detangling characteristics in shampoos.

The inclusion of betaines and amine oxides into liquid soaps in combination with alpha olefin sulfonates and amides ranging in size from $C_{12}$–$C_{18}$ at a pH under 7.0, effectively functions as a thickening agent in a liquid soap which leaves the hands soft and silky. Betaines with a preponderance of $C_{12}$ through $C_{14}$ groups have been shown to be effective foaming agents when used in combination with sodium lauryl sulfate, sodium lauryl ether sulfates and alpha olefin sulfonates.

Betaines as well as amine oxides with chain lengths ranging from $C_{16}$ through $C_{22}$ exhibit special effectiveness as thickening and conditioning agents. The introduction of a betaine of dimethyl oleyl betaine into a shampoo or body lotion does little to promote foam; however, viscosity of a resultant formulation with up to 2.0 percent of higher molecular weight chains such as oleyl, erucyl, arachidyl give significant thickening.

Betaines, amine oxides and quaternaries have been found to be extremely effective as tartar-removing agents in toothpaste formulations. A great deal of work had been done in this research arena in the early '70s. When betaines were introduced into toothpaste formulations, teeth were found to be "squeaky clean". However, a major drawback in using these compositions was the taste which was very difficult to mask with flavors. Consequently, as a result of this foul taste, no major brands of toothpaste were introduced to the marketplace. Numerous betaine derivatives were made but were never commercialized.

Betaines have also demonstrated properties of corrosion inhibition and have been incorporated into industrial formulations. The lower molecular weight betaines ranging from $C_6$ through $C_{18}$ have found wide use in industrial applications.

Another area in which betaines and amine oxides have been used in large volume with considerable success is in the oil and oil-field-related industry. As surfactants in the oil industry, betaines and amine oxides are used as emulsifiers, wetting agents, antifoulants, cleaners and detergents. With respect to paraffinic chemicals, betaines are used as surfactants for breaking up emulsions and as defoamers, for cleaning tanks, dispersing paraffins and as wetting agents for paraffinics. Betaines are also used in aqueous-isopropanol solutions to improve water injectivity in water flooding, as corrosion preventatives in floods, as a surfactant for clarification in water containing $H_2S$, to assist in the control of fouling due to microbial action, to enhance scale inhibition and also as an emulsifier and coupler in oil well formulations.

With the fairly recent concern with nitrosoamines which may be present as minor contaminants in widely used diethanolamide amines (derived from fatty acids as well as methyl esters), betaines and amine oxides have become used in extremely large quantities in consumer products such as shampoos, body baths, liquid soaps, etc.

OBJECTS OF THE INVENTION

It is an object of the present invention to provide novel betaine, amine oxide and quaternary compositions which can be used to improve or modify the characteristics of personal care products. Methods for improving or modifying the personal care products are another object of the present invention.

Secondary objects of the invention, depending upon the specific embodiment, may include one or more of the following:

A. To provide urethane polymers for use as conditioners, antistats, detanglers, facilitators for ease of wet/dry combing, to assist in the minimization of split ends (in hair products), as emulsifiers and for the maximization of color in colored hair products (dyes).

B. To introduce into hair and skin contacting formulations polymeric urethane surfactants that will maintain stability and become mildly cationic when used at a pH of less than about 7.0.

C. To increase the "adhesion" of the entire molecule to the hair and skin through the structure of the urethane linkages.

D. To provide a basis for "thickening" or increasing viscosity in given hair and skin contacting formulations as a result of the polymeric urethane structure of the surfactant molecule used.

E. To provide polymeric urethane surfactants for use as a cosmetic raw material in skin and hair contacting formulations to yield mildness and at the same time have low $LD_{50}$ values.

F. To introduce novel and unique polymeric betaines, amine oxides and quaternaries that are derived from, but not necessarily limited to, renewable vegetable sources making it possible to avoid bovine derived raw materials.

These and other objects of the present invention may be readily gleaned from the description of the invention which follows.

SUMMARY OF THE INVENTION

The present invention relates to polymeric urethane compounds, preferably derived from components obtained from naturally occurring sources.

The present invention relates to compounds of the formula:

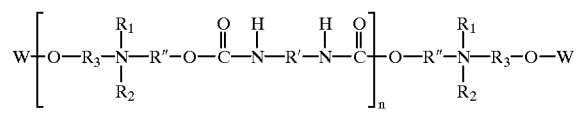

where R' is a $C_2$ through $C_{36}$ (preferably, $C_6$ through $C_{22}$) linear, cyclic or branch-chained saturated or unsaturated hydrocarbon group which is substituted or unsubstituted, monomeric or dimeric, an aromatic group, including a phenyl or benzyl group or substituted phenyl or benzyl group, an alkylphenyl, alkylbenzyl or substituted alkylphenyl or alkylbenzyl group; R" is selected from a $C_1$ through $C_{36}$ (preferably, $C_6$ through $C_{22}$) linear, branch-chained or cyclic saturated or unsaturated hydrocarbon group which is substituted or unsubstituted, monomeric or dimeric, a phenyl or benzyl group or substituted phenyl or benzyl group, an alkylphenyl, alkylbenzyl, substituted alkylphenyl or alkylbenzyl group, an alkylene oxide group $(R_4-O)_m$ where $R_4$ is a $C_2$ to $C_8$ alkylene group, preferably a $C_2$ to $C_6$ alkylene group, preferably a $C_2$ to $C_4$ unbranched alkylene group, more preferably a $C_2$ to $C_3$ alkylene or a mixture of $C_2$ and $C_3$ alkylene groups (preferably as polyethylene-co-polypropylene oxide blocks) and m is 2 to 150;

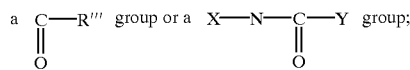

R''' is selected from a $C_1$ through $C_{36}$ (preferably, $C_6$ through $C_{22}$) linear or branch-chained, cyclic, saturated or unsaturated hydrocarbon group which is substituted or unsubstituted, monomeric or dimeric or an aromatic group, including a phenyl or benzyl group or substituted phenyl or benzyl group, an alkylphenyl, alkylbenzyl, substituted alkylphenyl or alkylbenzyl group; and $R_1$ is selected from a $C_1$ through $C_{36}$, preferably a $C_2$ through $C_{22}$ linear or branch-chained saturated or unsaturated hydrocarbon group which is substituted or unsubstituted, an aromatic group, including a phenyl or benzyl group or substituted phenyl or benzyl group, an alkylphenyl, alkylbenzyl, substituted alkylphenyl or alkylbenzyl group;

$R_2$ is a free electron pair (i.e., $R_2$ is not substituted, especially where R" is a

group),

O (to form N-oxide), a hydrogen or a quaternium group, or a mixture of hydrogen and quaternium groups, with the proviso that when $R_2$ is H and/or a quaternium group, the nitrogen to which said hydrogen or quaternium group is bonded is positively charged and forms a salt with a negatively charged counterion T;

$R_3$ is selected from a $C_1$ through $C_{36}$, preferably a $C_2$ through $C_{22}$, more preferably a $C_{10}$ to $C_{22}$ linear or branch-chained saturated or unsaturated hydrocarbon group which is substituted or unsubstituted, an aromatic group including a phenyl or benzyl group or substituted phenyl or benzyl group, an alkylphenyl, alkylbenzyl or substituted alkylphenyl or alkylbenzyl group or an alkylene oxide group $(R_4-O)_m$ where $R_4$ is a $C_2$ to $C_8$ hydrocarbon (alkylene) group, preferably a $C_2$ to $C_6$ hydrocarbon (alkylene) group, preferably a $C_2$ to $C_4$ unbranched hydrocarbon (alkylene) group, more preferably a $C_2$ to $C_3$ or a mixture of $C_2$ and $C_3$ (preferably as polyethylene-co-polypropylene oxide blocks) and m is an integer from 2 to 150;

each of X and Y is independently selected from a $C_1$ through $C_{36}$, preferably $C_1$ through $C_{22}$, even more preferably $C_1$ through $C_{10}$ linear, cyclic or branch-chained saturated or unsaturated hydrocarbon group which is substituted or unsubstituted, an aromatic group including a phenyl or benzyl group or substituted phenyl or benzyl group, an alkylphenyl, alkylbenzyl or substituted alkylphenyl or alkylbenzyl group;

n is an integer from 1 to 1000, preferably 2 to about 150, even more preferably about 2 to 20, even more preferably about 2–10; and even more preferably about 2 to 4;

W is H, a sulfosuccinate group or a $C_4$–$C_{10}$ alkyl sulfonate group, a phosphate group

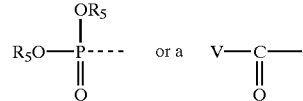

group where V is a $C_1$ through $C_{10}$ linear, cyclic or branch-chained saturated or unsaturated hydrocarbon group which is substituted or unsubstituted, a phenyl or benzyl group or substituted phenyl or benzyl group, an alkylphenyl, alkylbenzyl or substituted alkylphenyl or alkylbenzyl group and $R_5$ is a $C_1$ to $C_6$ alkyl group or a metal cation selected from the groups consisting of Na+, K+, Ca++ and Mg++ (preferably Na+ or K+).

In the compositions described above, $R_1$ is preferably an unsubstituted saturated or unsaturated branched or unbranched alkyl group, $R_2$ is preferably O to form an N-oxide with the adjacent nitrogen atom or a hydrogen or quaternium group, R" is preferably a

group or a

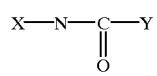

group;

X is preferably a $C_1$ to $C_4$ hydrocarbon group and Y is preferably a $C_6$ to $C_{22}$ linear or branch-chained saturated or unsaturated hydrocarbon which is even more preferably obtained from a naturally occurring fatty acid most preferably obtained from a plant source which contains a pendant hydroxyl group;

R'" is preferably a $C_6$ to $C_{22}$ linear or branch-chained saturated or unsaturated hydrocarbon which is even more preferably obtained from a narturally occurring fatty acid most preferably obtained from a plant source which contains a pendant hydroxyl group;

R' is preferably a saturated hydrocarbon containing pendant methyl groups, for example a substituted cyclohexyl group such as an isophorone group and W is most preferably H or a sulfosuccinate group or a related group containing an unsaturated double bond and optionally, an acid moiety (such as maleic acid which can be used to form a sulfosuccinate group) which may be modified to contain a sulfonate group.

In the present compositions, the quaternium group $R_2$ is a carbon containing group (generally, in order to form a quaternium group the nitrogen bonds to a carbon within the quaternium group) preferably selected from $C_1$ to $C_{10}$ alkyl groups, more preferably methyl and ethyl groups, benzyl and alkyl benzyl groups, among numerous others including substituted and unsubstituted saturated and unsaturated hydrocarbon groups including acetate groups (from chloroacetic acid), a propylene glycol group (from epichlorohydrin), ether groups and related groups, among numerous others.

Although the counterion T group may be any group which is anionic and is compatible with the chemistry of the present invention, when $R_2$ is H (the nitrogen to which the H is bonded forms a tertiary ammonium group), preferred T counterion groups include, for example, carboxylates (derived from carboxylic and polycarboxylic acids, preferably dicarboxylic acids, most preferably dicarboxylic acids such as dilinoleic acid, among others), anionic chloride, bromide and iodide, sulfates (mono-, di- and tri-anionic sulfate, preferably tri-anionic sulfate) and phosphates (mono-, di- and tri-anionic, preferably tri-anionic phosphate), among numerous others, with carboxylates and dicarboxylates being particularly preferred.

In the case where $R_2$ is a quaternium group as described generally hereinabove, counterion T is preferably anionic chloride, bromide, iodide, fluoride, sulfate (preferably mono- or di-anionic, preferably alkyl substituted monoanion such as methyl or ethyl sulfate, more preferably ethyl sulfate, especially where $R_3$ is an ethyl group) anionic chloride and sulfate (alkyl substituted mono-anionic sulfate) being the preferred counterion T. Monoanionic T groups may be represented by T⁻, and dianionic T groups are represented by T⁼.

Compositions which are representative of ammonium salts or quaternium salts (i.e., where $R_2$ is H or a quaternium group) according to the present invention described above may be further represented by the structure:

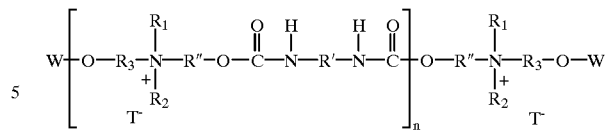

Where each of $R_1$, $R_2$, $R_3$, R', R", R'", T, V, W, X, Y and n is the same as described above.

Preferred embodiments of ammonium where T is derived from a dicarboxylic acid such as dilinoleic acid and which provide two carboxylate groups or moieties per molecule T, may be represented by the structure:

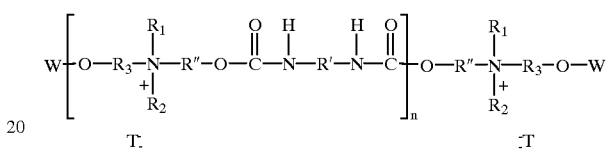

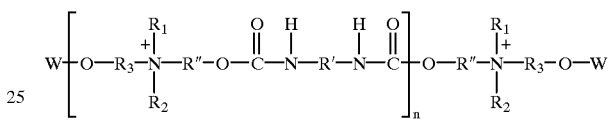

Where T is a dimer dilinoleate dianion.

Preferably, each of $R_1$, $R_2$, R" and R'" are linear or branched-chain saturated or unsaturated alkyl or alkylene groups which are derived or obtained from fatty acids or fatty amines of natural original, most preferably, fatty amines obtained from plant sources. Preferred hydroxyl containing acids for use in the present invention include ricinleic acid and dimethylolpropionic acid (which allows one to produce a dihydroxyl-substituted fatty amide fatty nd/or fatty amines for use in the present invention include, for example, soyamine, Substituents ("substituted") which may be used in the present compositions may include for example, halogens such as fluorine, chlorine and bromine, nitro groups, amine groups, substituted amine groups, hydroxyl groups, alkoxy groups, unsubstituted and substituted alkoxy groups, alkyl groups or substituted alkyl groups, among numerous others. Preferably, the substitutents in the present compositions are limited to halogen groups, most preferably fluorine and chlorine. One of ordinary skill in the art will be able to recognize modifications which readily may be made to the present compositions to instill desirable characteristics in the present compositions and to avoid undesirable reactions during polymerization such as chain termination, crosslinking and other reactions which may occur with reactive substituents such as hydroxyl groups and amines or amine-containing groups.

The groups $R_1$ and $R_3$ are preferably derived from such hydroxyl containing natural oils such as castor oil, or from tertiary amines containing alkoxide or alkylene oxide groups, the alkoxide groups preferably being linear and having chain lengths ranging from $C_6$ through $C_{22}$, and the alkylene oxide groups $(R_4-O)_m$, where $R_4$ is a $C_2$ to $C_8$ alkylene group and m ranges from 2 to 150 wherein a terminal hydroxyl group would be consumed in the reaction with diisocyanate to product a urethane. The tertiary amines could then be reacted to form betaines, amine oxides or salts, with the salts ranging in chain length from $C_6$ through $C_{50}$ carbon atoms.

The present invention also relates to compounds of the structure:

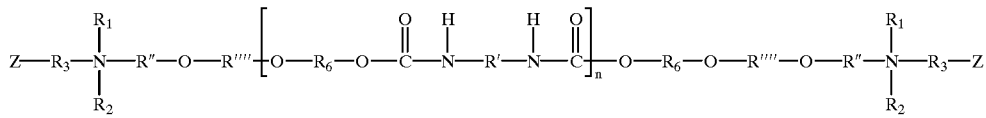

Where R'''' is a

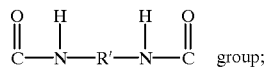 group;

$R_6$ is is selected from a $C_1$ through $C_{36}$, preferably a $C_2$ through $C_{22}$, even more preferably a $C_2$ to $C_{10}$ linear or branch-chained saturated or unsaturated hydrocarbon group which is substituted or unsubstituted, an aromatic group including a phenyl or benzyl group or substituted phenyl or benzyl group, an alkylphenyl, alkylbenzyl or substituted alkylphenyl or alkylbenzyl group or an alkylene oxide group $(R_4-O)_m$ where $R_4$ is a $C_2$ to $C_8$ hydrocarbon (alkylene) group, preferably a $C_2$ to $C_6$ hydrocarbon (alkylene) group, preferably a $C_2$ to $C_4$ unbranched hydrocarbon (alkylene) group, more preferably a $C_2$ to $C_3$ or a mixture of $C_2$ and $C_3$ (preferably as polyethylene-co-polypropylene oxide blocks) and m is an integer from 2 to 150;

Z is H or a $C_1$ through $C_{10}$ linear, cyclic or branch-chained saturated or unsaturated hydrocarbon group which is substituted or unsubstituted, a phenyl or benzyl group or substituted phenyl or benzyl group, an alkylphenyl, alkylbenzyl or substituted alkylphenyl or alkylbenzyl group; and each of $R_1$, $R_2$, $R_3$, R', R'', R''', T, V, X, Y and n is the same as described above.

Compounds of the present invention where $R_2$ is H and T is a dianionic species such as dilinoleic acid are clearly contemplated here.

Compounds according to the present invention exhibit primary utility as surfactants, wetting agents, anti-irritants, conditioners, viscosity builders in shampoos and liquid hand soaps. In addition, they assist in mending split ends of hair, have low levels of skin, eye and ingestion toxicity and can be used to disperse hair dyes and promote the hair dye function.

By selecting the diisocyanate, using the appropriate chain length, taking the degree of unsaturation in the backbone and by adjusting the degree of alkoxylation judicious use of either ethylene or propylene oxide), it is possible to introduce water solubility/insolubility or emulsification characteristics to the polymer.

By building a polymeric surfactant based on urethane technology, it is possible to offer a product that has substantivity to both the skin and hair based on the urethane bonds. Furthermore, adhesion and substantivity of the molecule may be enhanced by the cationic structure of the composition which, in certain embodiments which employs an amine which is converted to the ammonium salt, becomes more cationic with decreasing pH. Additionally, these polymeric urethanes are compatible with a wide array of surfactants that are commonly used in the cosmetic and toiletry industry such as amides, amine oxides, sulfosuccinates, sulfonates, sulfated castor oil, etc., since they share similar backbones.

Other properties and characteristics of the compounds of the present invention which make them highly desirable to the cosmetic and toiletry industry are as follows:

A. Extremely low order of toxicity and irritation
B. Low color
C. Low odor
D. Excellent compatibility in cosmetic formulations
E. Solubility with amides, sulfonates sulfosuccinates, and sulfobetaines
F. Nonrancidification
G. Coupling characteristics
H. Solubility in water, glycols and lower molecular weight alcohols
I. Ability to be synthesized to become insoluble in water, glycols and lower molecular alcohols (propoxylated versions)

DETAILED DESCRIPTION OF THE INVENTION

The following definitions shall be used throughout the specification in describing the present invention.

The term "personal care product" is used throughout the specification to describe a cosmetic or toiletry product which is preferably used on or in contact with the hair, skin and/or nails and which include effective concentrations of one or more of the compositions according to the present invention. Personal care products include, for example, cosmetics, floating bath oils, after shaves, creams, lotions, deodorants, including stick deodorants, pre-electric shave lotions, aftershave lotions, antiperspirants, shampoos, conditioners and rinses and related products, among others, including skin care products, eye makeups, body shampoos, protective skin formulations, lipsticks, lip glosses, after-bath splashes, pre-sun and sun products, including sunscreens. Virtually any chemical product which comes into contact with the hair or skin and which may include effective amounts or concentrations of one or more of the compositions according to the present invention may be considered a personal care product according to the present invention.

The term "surfactant" is used throughout the specification to describe compounds according to the present invention which contain a tertiary amine group which has been further reacted to form or otherwise forms an N-oxide group, a quaternary amine group or a carboxylate salt. Certain compounds according to the present invention are also referred to as urethane betaines, urethane N-oxides or urethane quaternary compounds because of the existence of at least one betaine group, N-oxide group or quaternary group (preferably more than two) and at least one urethane group (preferably, at least two).

The term "hydrocarbon" is used throughout the specification to describe various substituent groups according to the present invention. The term hydrocarbon embraces, but is not limited to, for example, alkyl, alkene groups (including those groups containg more than one unsaturated double bond), alkyne groups, aryl groups, aralkyl groups and related groups which are comprised of carbon and hydrogen atoms, such as alkylene groups (which are similar to alkyl groups except they are substituted at two carbons of the hydrocarbon with atoms or substituents other than hydrogen rather than one as is the case with alkyl groups) and related hydrocarbon radicals which may be found in the present compositions. In certain cases the terms "alkyl" (or related alkyl groups such as methyl, phenyl, benzyl, etc.) is used interchangeably with a di-substituted hydrocarbon group such as an alkylene, methylene, phenylene, etc. Hydrocarbons according to the present invention may be linear, cyclic or branch-chained, substituted (i.e., have pendant halogen, hydroxyl or other groups) or unsubstituted (i.e., comprised exclusively of C and H atoms) monomeric or dimeric (or even of higher order), aromatic, including phenyl or benzyl or substituted phenyl or benzyl group, alkylphenyl, alkylbenzyl or substituted alkylphenyl or alkylbenzy, etc.

The term "hydroxyl terminated" refers to an end group on the compositions according to the present invention which contains a free hydroxyl group at its terminal end. Although hydroxyl terminated groups are primarily and preferably primary hydroxyl groups, the terminal hydroxyl group may be found in a position such that the hydroxyl group is also a secondary or even a tertiary hydroxyl group. Hydroxyl terminated groups in compositions according to the present invention may be further reacted with carboxylic acids to form esters or isocyanates to form urethane groups as more fully described herein.

The term "tertiary amine" is used to describe an amine to which is attached at least three carbon-containing groups, each of the groups being covalently bonded to the amine group through a carbon atom within the group.

The terms "hydroxyl containing amidoalkyl dialkyl amine" or dialkoxyamine are used throughout the specification to delineate a linear, aromatic or branched chain hydrocarbon containing at least one hydroxyl group in the backbone or two hydroxyl groups as part of the dialkoxy functionality in the terminus of the molecule and may include such tertiary amidoamine compounds as diethoxyethylamine, diethoxypropylamine, dipropoxyethylamine, dipropoxypropylamine, bis-polyoxyethylene ranging from 2 to 100 units of ethylene oxide and bis-polypropoxyamine ranging from 2 to 100 units of propylene oxide.

The compounds may be unsubstituted or substituted (generally, halogen or hydroxyl substituted), but preferably only hydroxyl substituted. The linear backbone of the present invention may be totally saturated or contain exclusively single bonds (fully saturated) or at least one double or triple bond (unsaturated) which affect the solubility and viscosity of the final product.

The chain length of the present invention may range from 6 carbon atoms to 36 carbon atoms in the backbone with the preferred chain being in the range of 10 to 22 carbon atoms. The moles of alkoxylation may range from 2 to 150 moles that may be condensed on to the chain length ranging from 6 to 36 carbon atoms.

Furthermore, it is possible to vary the ethylene oxide propylene oxide ratios from 1 to 99 percent ethylene propylene oxide and conversely to vary the ratio of 99 to 1 of the ethylene propylene oxide which will affect properties of solubility, viscosity and emulsification properties.

The term "diisocyanate" is used throughout the specification to describe a linear, cyclic or branch-chained hydrocarbon having two free isocyanate groups. The term "diisocyanate" also includes halogen substituted linear, cyclic or branch-chained hydrocarbons having two free isocyanate groups. Exemplary diisocyanates include, for example, isophoronediisocyanate, m-phenylene-diisocyanate, p-phenylenediisocyanate, 4,4-butyl-m-phenylene-diisocyanate, 4-methoxy-m-phenylenediisocyanate, 4-phenoxy-m-phenylenediisocyanate, 4-chloro-m-phenyldiisocyanate, toluenediisocyanate, m-xylylenediisocyanate, p-xylylenediisocyanate, 1,4-napthalenediisocyanate, cumene-1,4-diisocyanate, durenediisocyanate, 1,5-napthylenediisocyanate, 1,8-napthylenediisocyanate, 1,5-tetrahydronapthylenediisocyanate, 2,6-napthylenediisocyanate, 1,5-tetrahydronapthylenediisocyanate; p,p-diphenylenediisocyanate; 2,4-diphenylhexane-1,6-diisocyanate; methylenediisocyanate; ethylenediisocyanate; trimethylenediisocyanate, tetramethylenediisocyanate, pentamethylenediisocyanate, hexamethylenediisocyanate, nonamethylenediisocyanate, decamethylene-diisocyanate, 3-chloro-trimethylenediisocyanate and 2,3-dimethyltetramethylenediisocyanate, among numerous others. Isophorone diisocyanate is used the preferred diisocyanate used in the present invention.

The term "carboxylic acid" as used herein describes organic acids which may contain one or more carboxylic acid moieties preferably ranging in size from $C_2$ to $C_{50}$ or more. The term "monocarboxylic acid" is used to describe organic acids which contain only one carboxylic acid moiety. The term "polycarboxylic acid" is used to describe organic acids which contain at least two carboxylic acid moieties. Those polycarboxylic acids which contain only two carboxylic acid moieties may also be referred to in this specification as "dicarboxylic acids".

Exemplary carboxylic acids for use in the present invention include, for example, pentanoic acid, neopentanoic acid, caproic acid, caprylic acid, capric acid, heptanoic acid, neoheptanoic acid, octanoic acid, iso-octanoic acid, 2-etlhylhexanoic acid, nonanoic acid, isononanooic acid, decanoic acid, iso-decanoic acid, neodecanoic acid, undenanoic acid, undecylenic acid, lauric acid, isolauric acid, myristic acid, palmitic acid, stearic acid, hydroxy stearic acid, isostearic acid, arachidonic acid, tallow fatty acid, arachidic acid, behenic acid, lignoceric acid, lauroleic acid, myristoleic acid, palmitoleic acid, olelic acid, gadoleic acid, erusic acid, ricinoleic acid, linolenic acid, linoleic acid, lactic acid, glycolic acid, mandelic acid, eicosopentaoic acid, phenylstearic acid, retinoic acid, salicylic acid and benzoic acid, among numerous others, including dimer acids, trimer acids, adipic acid, azealeic acid, malic acid, succinic acid, dodecandioic acid, citric acid, tartaric acid, sebacic acid, fumaric acid, glucaric acid, glutaric acid and oxalic acid, among others.

Preferred polycarboxylic acids for use in the present invention include, for example, $C_2$–$C_{50}$ dicarboxylic acids, including dimer, trimer and tetramer acids which are made from the dimerization, trimerization or tetramerization of long-chain unsaturated acids, such as linoleic acid, among numerous other acids, including mixtures of these acids, more preferably including $C_5$–$C_{37}$ dicarboxylic acids and mixtures of these acids. Dilinoleic acid is a preferred dicarboxylic acid. Other acids which may be preferably used in the present invention include, for example, adipic acid, azealeic acid, malic acid, succinic acid, dodecandioic acid, citric acid, tartaric acid, sebacic acid, fumaric acid, glucaric acid, glutaric acid and oxalic acid, among others. Preferred dicarboxylic acids containg carboxylic groups at the terminal ends of the molecule.

Other exemplary polycarboxylic acids include, for example, polymeric products containing carboxylic (carboxylate) side chains, such as acrylic or (meth)acrylic, polyesters, cellulosic polymers, polyvinyl alcohol, polysiloxanes, oligo and polypeptides, among numerous others.

Carboxylic acids may be used in the present invention to neutralize tertiary amines to function as counter ion (T) in the ammonium salt which is formed during neutralization of the free amine groups. Alternatively, carboxylic acids, especially fatty acids obtained from natural sources, may be used advantageously to prepare the tertiary amines or amidoamines which may be used to prepare compositions according to the present invention.

The term "quaternizing agent" is used throughout the specification to describe compounds which are used to react with tertiary amines to produce quarternary salts according to the present invention. Quaternary salts are salts which are produced when a tertiary amine is reacted with a quaternizing agent to produce a quaternary amine (quaternium) which is substituted with four carbon-containing groups. The quaternary amine produced is cationic and is generally found complexed with an anionic group or "counterion", which is generally derived from the quaternizing agent used to produce the quaternary amine. Exemplary quaternizing agents for use in the present invention include, for example, dimethyl sulfate, diethyl sulfate, methyl bromide, benzyl chloride, ethyl benzyl chloride, methyl benzyl chloride, dichloroethyl ether, epichlorohydrin, ethylene chlorohydrin, methyl chloride, pyridinium chloride and allyl chloride, among others, such that the group reactive with the amine produces an N—$R_3$ group with the amine and the positively charged quaternary amine group is complexed with an anionic group or counterion, which is represented as $T^-$. The counterion may be any group which is anionic and is compatible with the chemistry of the present invention and preferably is an anionic chloride, bromide, iodide, fluoride, carboxylate (from, for example the use of chloroacetic acid or sodium monochloroacetate as the quaternizing agent to provide an acetate which can provide both a quaternium group as well as the counterion) sulfate (mono- or di-anion, preferably alkyl substituted mono-anion such as methyl or ethyl sulfate, more preferably ethyl sulfate) and phosphate (mono-, di- and tri-anion, preferably tri-anion), among numerous others, with anionic chloride and sulfate (alkyl substituted mono-anion) being the preferred counterion T.

The term "alkylene oxide" refers to a polymeric group of repeating units of the general formula $(R_7-O)_n$— where $R_7$ is a $C_2$ to $C_8$ alkyl group, preferably a $C_2$ to $C_6$ alkyl group, preferably a $C_2$ to $C_4$ unbranched alkyl group, more preferably a $C_2$ to $C_3$ or a mixture of $C_2$ and $C_3$ (preferably as polyethylene-co-polypropylene oxide blocks) unbranched alkyl groups and n ranges from 2 to 150 units (corresponding to 2 to 150 moles of alkylene oxide) within that group. Most preferably, $R_7$ is $C_2$ (ethylene oxide).

The term "surfactant" is used throughout the present invention to describe compounds which reduce surface tension, condition, emolliate, prevent flyaway hair, function as antistats, emulsify, solubilize hair dyes (colors), assist in the reduction of split (hair) ends, are of a low order of toxicity, assist in detangling hair, give excellent wet/dry hair properties, function as anti-irritants, viscosity builders, and because of the urethane functionality, increase adhesion to the hair shaft; as well as soften and emolliate the skin. It is an unexpected result that the present compositions may be varied to accommodate numerous physicochemical characteristics in a single composition.

The term "emolliate" or "emollient" is used throughout the specification to describe concentrations of amounts of compound of the present invention which are included in the personal care products to provide emolliency to skin contacting formulations such as body shampoos, liquid soaps, body conditioners, toners and effective emollient properties for treating epithelial tissue. Such amounts may range from as little as 0.05% to 15% by weight or more of the personal care products according to the present invention.

The term "effective amount" is used throughout the specification to describe concentrations or amounts of compounds according to the present invention which are effective in conveying desired characteristics such as conditioning, adhesion, softening, prevention of static electricity buildup, the promotion of wet and dry hair combability, detangling of hair, solubilization and compatibility with other surfactants, promotion of viscosity, reduction of toxicity, promotion of color solubilization, minimization of split hair ends, etc. to a formulation in the cosmetic, toiletry or personal care industry.

Compounds as outlined in the present invention may be prepared by synthetic methods known in the art. Generally speaking, a general procedure involves the reaction of a monofunctional or difunctional hydroxy fatty amine (for example, ricinoleylamide containing glycerine or bis-alkoxy amino or polyalkoxyamino or polyhydroxy functional product) based on a linear, iso or aromatic chain, with a diisocyanate in the presence of heat and either an amine or tin catalyst such as stannous octanoate. Each isocyanate moiety is thereby converted to a urethane moiety while maintaining the presence of "free and unreacted" tertiary amines. These "free" tertiary amines may then quaternized, i.e., reacted with, with for example, sodium monochloracetate, chloracetic acid in the presence of sodium of potassium hydroxide to form the resulting betaine. The free tertiary amines described above may also be reacted with other quaternizing agents as otherwise described herein to produce quaternary amines surfactants. Alternatively, the tertiary amine may simply be reacted with a carboxylic acid to form a tertiary ammonium salt with a carboxylate counterion. In addition, the "free" tertiary amines may be reacted with hydrogen peroxide or another oxidizing agent to form amine oxides which can be used in the cosmetic, toiletry and personal care industry in skin and hair contacting formulations.

By way of example, an amido amine containing at least one free hydroxyl group (preferably at least two hydroxyl groups) may be prepared from castor oil or any related hydroxyacid. The free hydoxyl groups may then be reacted with a diisocyanate to produce a oligomeric or polymeric urethane composition which contains a tertiary amine group. The tertiary amine group may then be quaternized, acidified (with a carboxylic acid or a related acid to produce a sulfate, phosphate or chloride salt) or oxidized to produce the corresonding quaternary amine salt, ammonium salt or N-oxide containing composition. Alternatively, alkoxylated fatty amines such as soyamine, oleylamine and cocamine or related alkoxzylated fatty amines which contain at least two hydroxyl groups, among others, may be prepared and then reacted with diisocyanates to produce an oligo or (poly) urethane composition, which may be further reacted to produce the quaternary amine salt, ammonium salt or N-oxide containing composition.

The terminal hydroxyl groups in any of the above compsitions may be esterified or otherwise end-capped with carboxylic acids such as maleic acid and related unsaturated acids to produce an unsaturated ester group (preferably having 1,4-enone which is activated to form a sulfonate) which can be further derivatized to an alkyl sulfonate ester or salt with sodium bisulfite or a related sulfonating agent. Preferably, these alkyl sulfonates are $C_4$–$C_{10}$ alkyl sulfonate groups. Alternatively, the compositions may be end-capped with a phosphate group or other group which is anionic.

Compounds as outlined in the present invention may be used as conditioners for keratinous and epithelil tissue such as hair, nails and skin. By the introduction of conditioners and hair softening amounts of the polymeric urethane betaines, it is possible to introduce effective personal care, toiletry and cosmetic products that will achieve highly desirable characteristics.

Effective amounts of the surfactants of polymeric urethanes of the present invention may also function as coupling and clarifying agents in formulations in the personal care, toiletry and cosmetic industry, where glycols with their inherent viscosity reduction properties have been used in the past. In numerous instances, the novel betaine urethane polymers have effectively replaced ethoxylated sorbitan monoesters of lauric and/or oleic acids for their clarification, coupling and solubilization properties. Additionally, the products of the present invention are naturally derived, are biodegradable and are compatible with biological systems and demonstrate a low order of toxicity and irritation.

The present compounds inherently bestow upon a cosmetic formulator the ability to achieve a wide range of desirable end characteristics that may be sought in a given formulation by selecting polymeric urethanes according to the present invention and adding it to a composition to be improved or modified. Indeed, it is an unexpected result of the present invention that personal care products may have at least two characteristics, and often, more than two characteristics of the formulation substantially modified by the introduction of a single composition. For example, with the increase in the degree of ethoxylation of an ethoxylated tertiary amine, it is possible to achieve increased water solubility and increased viscosity. By selecting a backbone with increased unsaturation, it is possible not only to increase water solubility but also to decrease viscosity of the polymeric urethane betaine. The higher the degree of unsaturation present in the molecule, the greater the effectiveness of softening, conditioning., prevention of flyaway hair and increased benefits of wet and dry combing, etc. As one increases both the number of urethane groups within the composition, the molecular weight of the composition will increase as will the viscosity (generally) and ability of the compsoition to adhere to keratinous tissue. Those of ordinary skill engaging in routine experimentation will be able to determine the preferential chain lengths for optimum results. Beneficial characteristics for foaming are to be found in the $C_{12}$ through $C_{18}$ chain lengths. Chain lengths primarily ranging from $C_{18}$ through the $C_{22}$ area will tend to have a greater effect upon viscosity of a given formulation.

Compositions according to the present invention may be used to formulate skin and hair contacting formulations in the cosmetic, toiletry and personal care industries that have excellent aesthetics heretofore unachievable.

It has also been unexpectedly discovered that the polymeric urethanes of the present invention derived from hydroxyl containing long chain isomeric or aromatic tertiary amines when reacted to form surfactants such as betaines or amine oxides or reacted with long chain fatty acids ranging in chain length from $C_6$ through $C_{36}$ or dimerized with dimer or trimer acids that the properties achievable from an aesthetic viewpoint far surpass those properties that alone can be ascribed to the polymeric urethanes of hydroxyl containing long chain, isomeric or aromatic tertiary amines themselves. In essence, the surfactants derived from hydroxyl containing long chain linear, isomeric or aromatic tertiary amines far surpass the properties of emulsification, detangling, conditioner, softening, prevention of flyaway hair, antistatic characteristics, facilitation of wet and dry hair combing, repair of split ends (hair). Further, the surfactants so derived also assist in hair colorization and are of a low order of dermal and ocular toxicity. The combination of characteristicds which can be instilled in a personal care product using a single composition according to the present invention without relying on numerous additives is unexpected. That all of these characteristics could be instilled with a substantial absence of toxicity is particularly unexpected.

It has been further surprisingly discovered that the polymers of the present invention are excellent hair conditioners and show effectiveness in the following systems:

Shave creams

Women's toiletries for shaving preparations

Depilatories

Relaxers

Conditioners 2-in-1 shampoos

Furthermore, the present invention provides the following personal care formulations:

Unexpectedly and dramatically reduces split ends in conditioning and shampoo formulations;

Provides good wet/dry combing;

Provides body and shine to hair;

Reduces tangles and provides a more manageable base for styling;

Softens coarse hairs to provide easier shaving;

Provides a closer, less damaged shave.

In general, compositions according to the present invention are included in personal care products/formulations in effective amounts, i.e., amounts which produce an intended effect. The amount of composition generally ranges from about 0.05% to about 15% by weight or more of personal care formulations according to the present invention. In preferred embodiments of emulsion-based foromulations, compositions according to the present invention are included in amounts ranging from about 0.1% to about 5% by weight. In the case of shampoos and conditioners, compositions according to the present invention are included in amounts ranging from about 0.1% to about 3% by weight of the formulation.

For example, in shampoos, rinses, conditioners, hair straighteners, hair colorants and permanent wave formulations, the compositions according to the present invention preferably comprise about 0.1% to about 20% by weight, more preferably about 0.25% to about 3% by weight of the final end-use hair-care composition. Other components which may be included in hair-care formulations include, for example, a solvent or diluent such as water and/or alcohol, other surfactants, thickeners, coloring agents, preservatives, additional conditioning agents and humectants, among numerous others.

In the case of shave creams and gels, after-shave lotions and shave-conditioning compositions (for example, pre-electric shave formulations), the compositions according to the present invention are included in amounts ranging from about 0.25% to about 15% or more by weight, more preferably about 0.5% to about 10% by weight. Other components which may be included in these end-use compositions include, for example, water, and at least one or more of emollients, humectants and emulsifiers and optionally, other conditioning agents, medicaments, fragrances and preservatives.

In the case of skin lotions and creams, the present compositions are included in amounts ranging from about 0.25% to about 15% by weight, more preferably, about 0.5 to about 10% by weight. Additional components which may be employed in these compositions include, for example, water, emollients and emulsifers and optionally, other conditioning agents medicaments, fragrances and preservatives.

In the case of sunscreens and skin-protective compositions, the present compositions are included in amounts ranging from about 0.25% to about 15% or more by weight, preferablyt about 0.5% to about 7.5% by weight of the final formulations. Additional components which may be employed in these compositions may include, for example, a UV absorbing composition such as para-amino benzoic acid (PABA) or a related UV absorber or a pigment such as $TiO_2$, water or oil, and optional components including, for example, one or more of an oil, water, suspending agents, other conditioning agents and emollients, among others.

In the case of bar and liquid soaps, compositions according to the present invention are included in amounts ranging from about 0.25% to about 20% by weight or more, preferably about 0.5% to about 10% by weight. Additional components which may be included in bar and liquid soaps include water and surfactants and optionally, bacteriacides, fragrances and colorants, among others.

When the present invention was tested in a shave cream as compared to commercially available products, it was reported that 24 of our of 25 participants preferred the shave cream incorporating the present invention, with only one participant being undecided for the following:

Closeness of shave

Less Damage

Softer skin feel

Longer lasting fragrance

Smoother shave

Ease of shave

It was surprisingly discovered that when the present invention was introduced into 2:1 conditioning shampoos and into hair conditioners, results indicated that the present invention yielded excellent conditioning of damaged hair; and, in fact, performed better than commercially available products on the marketplace. A panel composed of 35 individuals selected formulations at close to 90% over products that are commercially available. Furthermore, the present invention when incorporated into both shampoos and conditioners, the following unforeseen effects were observed:

Better "feel"

Better appearance

Increased viscosities

Also, emulsion formulations performed better than normal allowing the formulator to reduce the maximum temperature of the phases, thereby decreasing manufacturing time and, in effect, reducing costs.

The following examples of compounds (and their proposed INCI names) according to the present invention have been prepared:

The reaction product of dimethylaminopropyl ricinoleamide with isophorone diisocyanate (IPDI) and sodium monochloracetate FOAMTAINE PPI-RC;

INCI Name: Recinoleamidopropyl Dimethyl Glycine/ IPDI Copolymer

The reaction product of bis-polyoxyethylene (15) soyamine with IPDI and sodium monochloracetate. FOAMTAINE PPI-SA-15

INCI Name: PEG-15 Soyamine Bis Hydroxethyl Glycine/ IPDI Copolymer

The reaction product of bis-polyoxyethylene (15) amine with IPDI and sodium monochloracetate FOAMTAINE PPI-CA- 15

INCI Name: PEG-15 Cocamine Bishydroxyethyl Glycine/IPDI Copolymer

The reaction product of bis-polyoxyethylene (15) tallow amine with IPDI and sodium monochloracetate FOAMTAINE PPI-TA INCI Name: PEG-2 Tallowamine Bishydroxyethyl Glycine/IPDI Copolymer The reaction product of bis-hydroxyethyl(2) Soyamine/ IPDI Copolymer with Hydrogen Peroxide FOAMOX PPI-SA INCI Name: N-Soyamine N,N-Bishydroxyethyleamine Oxide/IPDI Copolymer The reaction product of bis-hydroxylethyl (2) Soyamine IPDI Copolymer and Diethyl sulfate FOAMQUAT PPI-SA INCI Name: N-Soyamine N,N-Hydroxyethyl N-Ethyl Ammonium Ethyl Sulfate/IPDI Copolymer The reaction product of bis-Hydroxyethyl (15) Soyamine/ IPDI Copolymer and Diethyl sulfate FOAMQUAT PPI-CA-15

INCI Name: PEG-15 Cocamine-N-Ethyl Ammonium Ethyl Sulfate/IPDI Copolymer

The reaction product of bis-Hydroxyethyl (2) Soyamine/ IPDI Copolymer and Dimer Dilinoleic acid POLYDERM PPI-SA-D INCI Name: PEG-2Soyamine/IPDI Copolymer Dimer Dilinoleate The reaction product of bis-Hydroxyethyl (2) Soyamine and IPDI POLYDERM PPI-SA INCI Name: Di-PEG-2 Soyamine/IPDI Copolymer The reaction product of Polyoxyethylene (15) Cocamine and IPDI POLYDERM PPI-CA-15

INCI Name: PEG-15 Cocamine/IPDI Copolymer

The reaction product of Recinoleamidopropyl Dimethyamine and Glycerine with IPDI POLYDERM PPI-RC INCI Name:Ricinoleamidopropyl DimethylAmine-Glyceryl/IPDI Copolymer The reaction product of Ricinoleyamidopropyl Dimethyamine and Glycerine with IPDI POLYDERM PPI-RCD INCI Name: Recinoleamidopropyl DiumethylAmine-Glyceryl/IPDI Copolymer Dimer Dilinoleate Structural formulas of the above-described surfactants and other surfactants according to the present invention are presented herein.

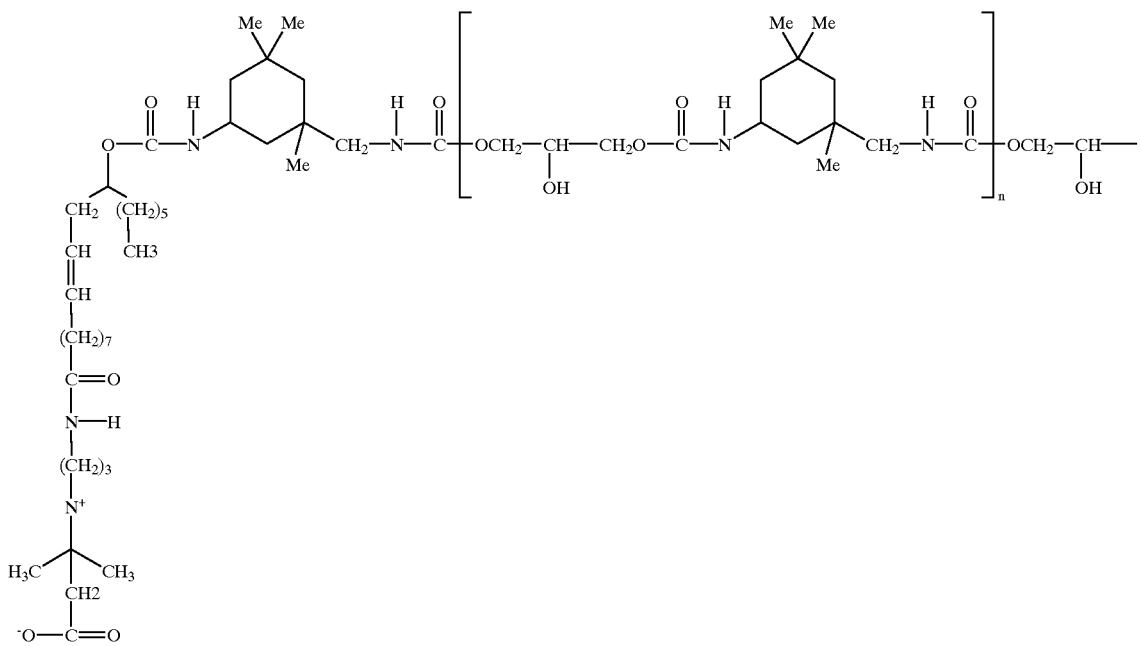
FOAMTAINE PPI-RC
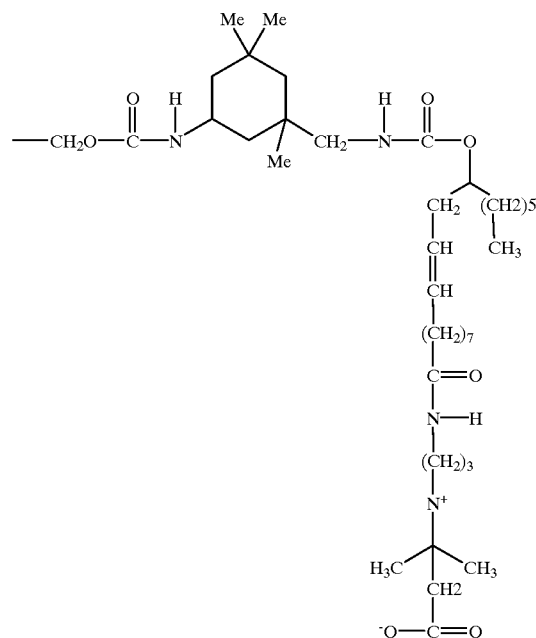
FOAMTAINE PPI-SA-15
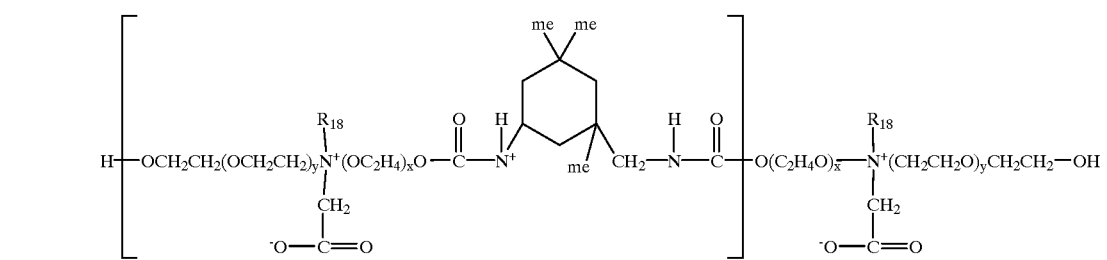
x + y = 15

-continued
FOAMTAINE PPI-CA-15
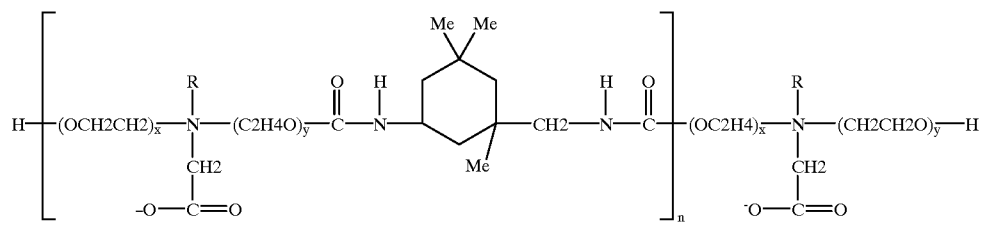
x + y = 15
FOAMOX PPI-SA
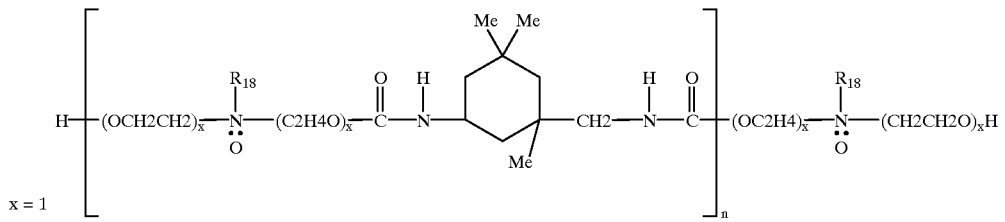
x = 1
FOAMQUAT PPI-SA
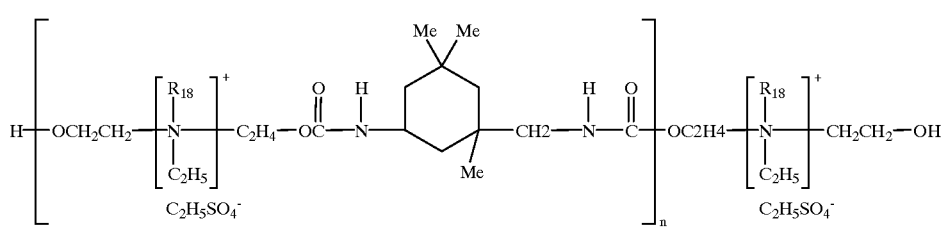
POLYDERM PPI-SA-D
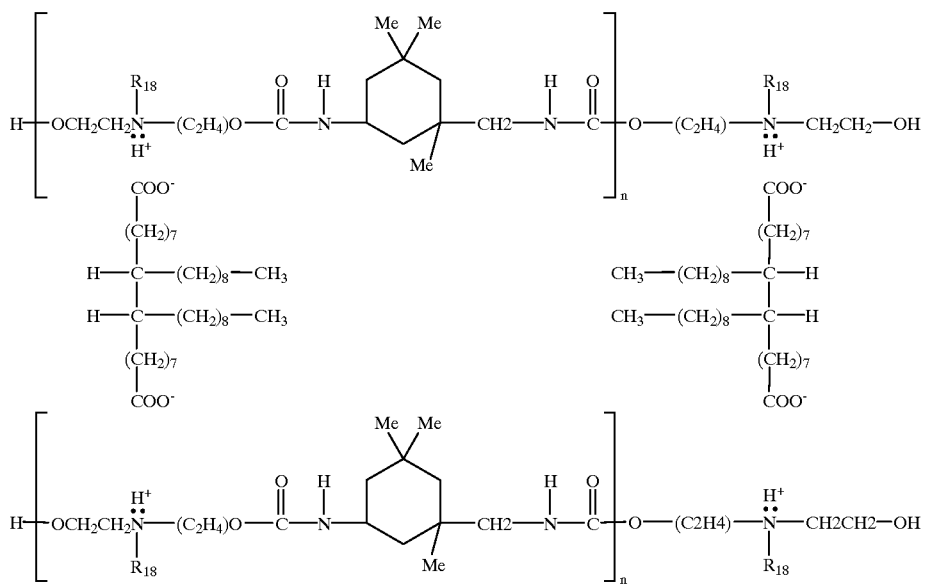
FOAMQUAT PPI-CA-15
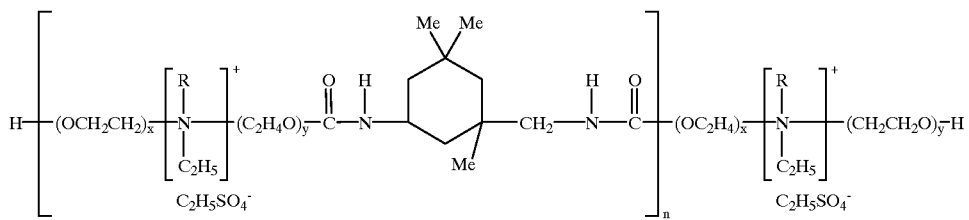

POLYDERM PPI-SA
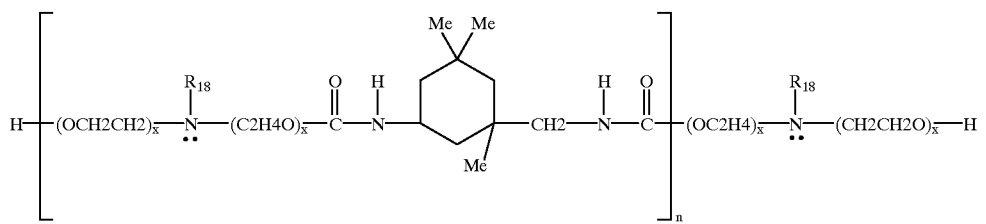
POLYDERM PPI-CA-15
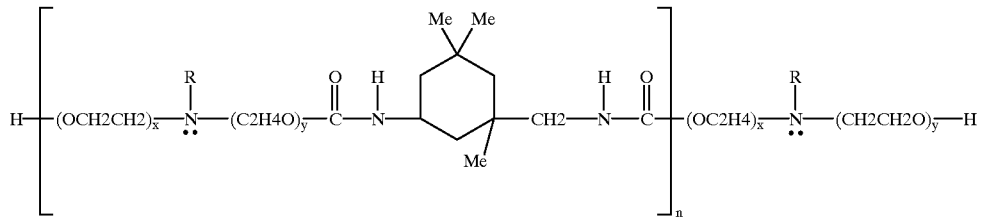
POLYDERM PPI-RC
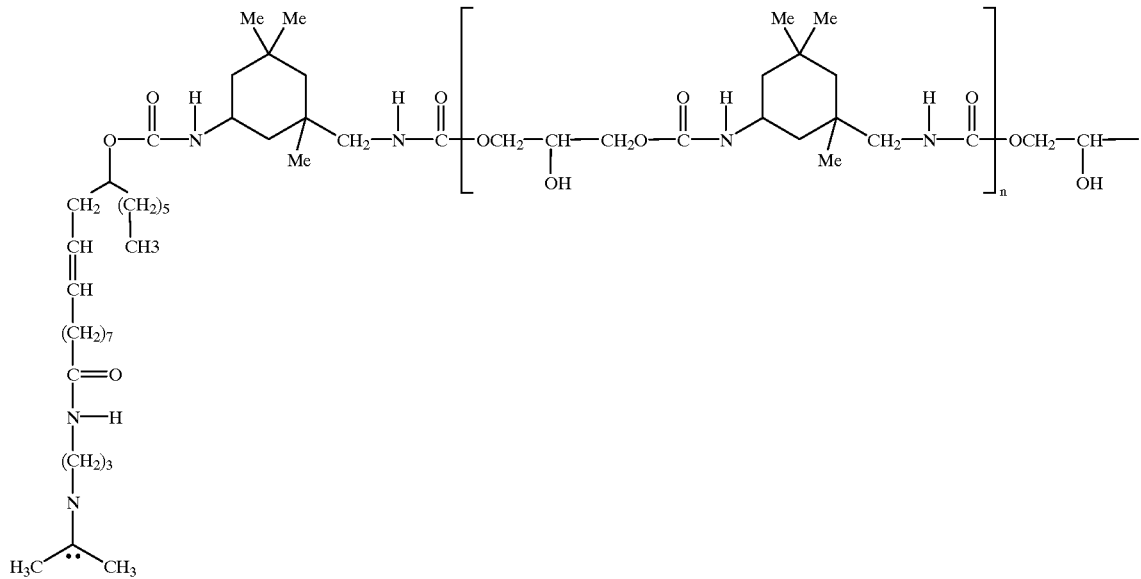
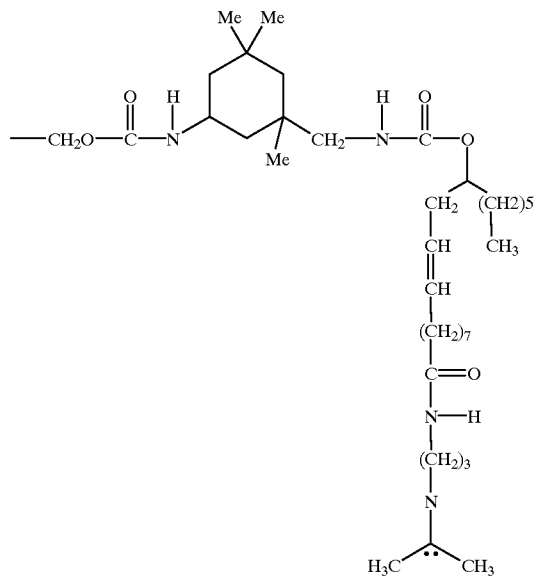

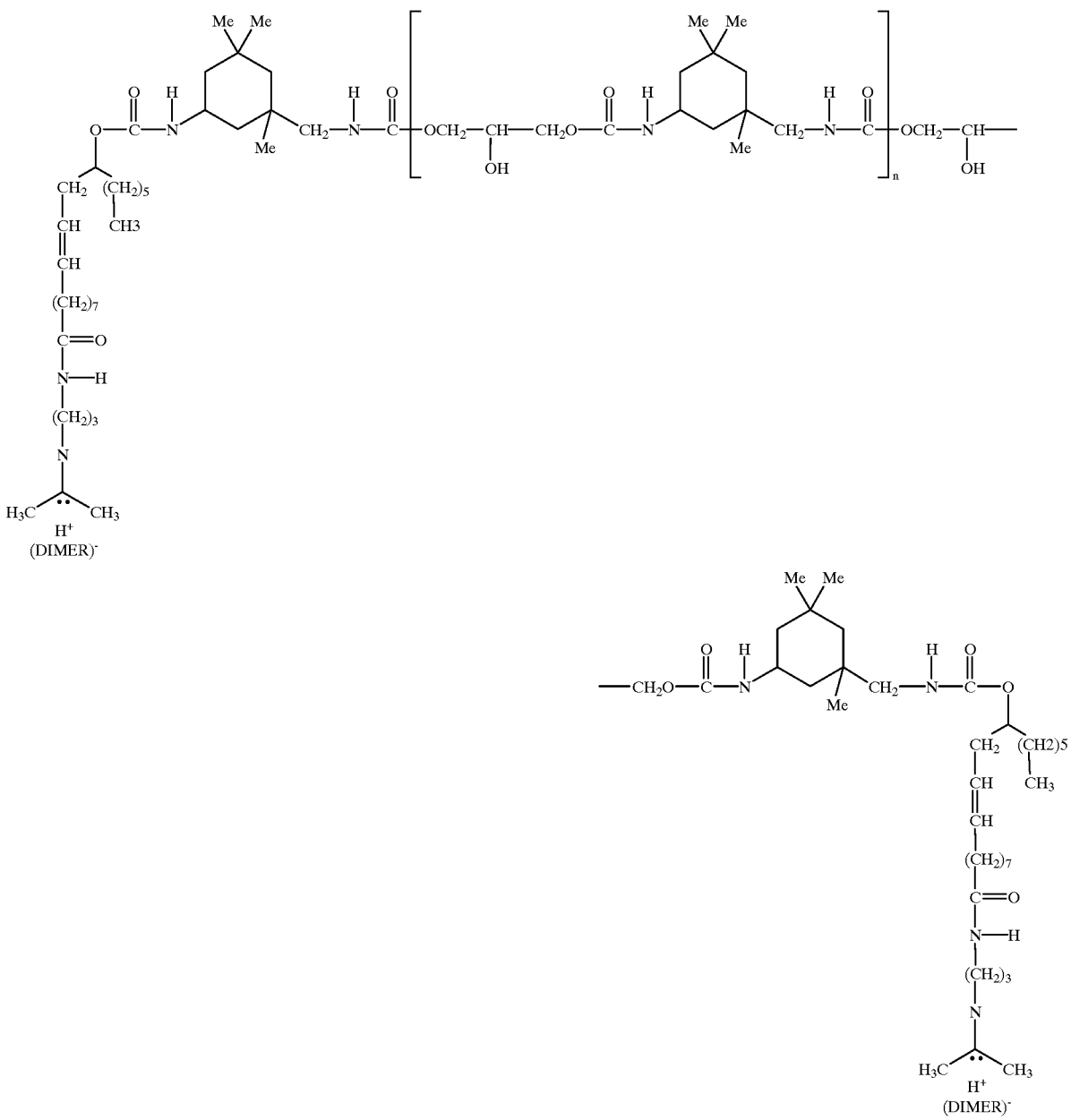

POLYDERM PPI-RCD

The present invention is now described, purely by way of illustration, in the following examples. It will be understood by one of ordinary skill in the art that these examples are in no way limiting and that variations of detail can be made without departing from the spirit and scope of the present invention.

EXAMPLES

Materials and Methods

In performing the following syntheses and preparing the following final formulations, the reagents which are used are indicated in the specific examples. Solvents, where used, are preferably distilled prior to use. Sources of other materials are indicated in the appropriate experimental section. In most instances, although not in every instance, trademarked materials are available from Alzo, Inc., Sayreville, N.J.

Laboratory Procedures

Example 1

Laboratory Procedure for N-Recinoleamidopropyl-N,N-Dimethyl Glycine Dimer with IPDI Copolymer 1. Into a 2 liter flask, introduce 1,415 grams of ricinoleamido-propyldimethyl amine and bring to a temperature of approximately 70° C.
2. Into a separate 3 liter flask, introduce 300 grams of sodium monochloracetate containing 2,160 grams of deionized water.

3. Bring the SMCA/deionized water solution to a temperature of 70° C. and add the n-ricinoleamidopropyldimethyl amine. (An emulsion will initially form [water in oil]).
4. Raise the temperature to approximately 85–90° C. and continue to hold until clarity is achieved.
5. Continue to stir until a pH of 5–7 on an as-is-basis is reached.

Example 2

Laboratory Procedure for N-Recinoleamidopropyl-N,N-Dimethyl-N-Ethyl Ammonium Ethyl Sulfate/ IPDI Copolymer 1. Into a clean 2 liter three-neck flask, charge 1,425 grams of n-ricinoleamidopropyl dimethylamine with 152 grams of propylene glycol.
2. Stir until uniform and heat to a temperature of 80–85° C.
3. Shut off the heating mantle and then begin a slow addition of diethyl sulfate being careful to control a potential exotherm. (Cooling may be required).
4. After the entire amount of diethyl sulfate has been added, maintain a temperature of 80–85° C.
5. Continue to check the free amine until a value of 1.0 Max. has been reached. At that point, the reaction has been completed and the product has been made.

Formulary

Pre-Electric Shave Lotion

Example I

| INGREDIENTS | %, WEIGHT |
| --- | --- |
| Bis-Hydroxyethyl Soyamine/ IPDI Polymer* | 0.5 |
| Diisopropyl Adipate* | 10.0 |
| Ethanol, SD-40, 200 Proof | 60.0 |
| Boric Acid | 1.0 |
| Fragrance | 0.5 |
| Deionized Water | 28.0 |
| Total | 100.0 |

*From Alzo, Inc. Sayreville, New Jersey

Procedure

1. Into a clean vessel add ethanol, diisopropyl adipate and Bis-Hydroxyethyl Soyamine/IPDI Polymer and stir until homogeneous (Part A).
2. Solubilize Boric Acid into the Deionized water in a separate vessel (B).
3. Pump B into A and add perfume.

Results: The above-described Pre-Electric Shave Lotion is applied to a bearded face and permitted to dry before shaving with an electric shaver. The result is an exceptionally smooth shave with little or no friction from cuts, scratches or knicks. The incorporation of Bis-Hydroxyethyl Soyamine/IPDI Polymer leaves the skin soft and smooth for hours.

Shampoo—Natural Conditioning

Example II

| INGREDIENTS | %, WEIGHT |
| --- | --- |
| Deionized Water | 48.5 |
| Bis-Hydroxyethyl Tallow Amine/ IPDI Amine Polymer[1] | 1.5 |
| Cocoamidopropyl Betaine, 35%[1] | 20.0 |
| Disodium Oleamido PEG-2 Sulfosuccinate | 10.0 |
| Sodium Laureth Ether[2] | 20.0 |
| Preservative | q.s. |
| Fragrance | q.s. |
| Total | 100.0 |

[1]Alzo, Inc.
[2]Stepan

Procedure

1. Into a clean mixing tank add the water and heat to approximately 60° C. Add with slow agitation the soldium laureth sulfate, followed by Bis-Hydroxyethyl tallow amine/IPDI Copolymer, Cocoamidopropyl Betaine and finally the Disodium Oleamido PEG-2 Sulfosuccinate.
2. Add the preservative at 50° C.
3. Mix thoroughly, cool and add remaining fragrance and water.

Result: Hair is left soft, free from tangles, manageable and easy to comb (wet and dry) with no flyaway hair.

Mild Skin Cleansing Bar

Example III

| INGREDIENTS | %, WEIGHT |
| --- | --- |
| Sodium Cocoyl Isethionate[1] | 56.8 |
| Dimethylamidopropyl Amine Ricinoleate/[2] IPDI Polymer Betaine | 13.4 |
| Bis-Hydroxyethyl Soyamine/IPDI Polymer[2] | 1.0 |
| Stearic Acid[3] | 12.0 |
| Coconut Fatty Acid[3] | 3.5 |
| Sodium Isethionate[1] | 0.9 |
| Sodium Chloride | 0.7 |
| Fragrance | 0.1 |
| Deionized Water | 5.3 |
| Total | 100.0 |

[1]FineTex, Inc.
[2]Alzo, Inc.
[3]Akzo-Nobel

Procedure

1. To a clean mixing vessel, add the Sodium Cocoyl Isoethionate with the Dimethylamidopropyl Amine Ricinolate/IPDI Polymer Betaine and Bis-Hydroxyethyl Soyamine/IPDI Polymer. Heat this mixture to 65° C. (Part A).
2. Into a separate vessel, add stearic acid, cocoanut fatty acid and heat to 70° C. (Part B).
3. Pump part B into A and add deionized water and perfume.
4. Continue agitation to homogeneity.
5. Fill into molds at 60° C.

Transparent Facial Cleansing Bar

Example IV

| INGREDIENTS | %, WEIGHT |
|---|---|
| Transparent Tallow Soap Stock*[1] | 20.0 |
| Coconut Oil** | 15.0 |
| Castor Oil*** | 3.0 |
| Corn Oil** | 3.0 |
| Sodium Hydroxide | 7.0 |
| Ethyl Alcohol | 23.0 |
| Sugar | 11.0 |
| Bis-Hydroxyethylsoyamine/IPDI Polymer Betaine*** | 2.0 |
| Deionized Water | q.s. 100.0 |

*Uniquema
**Alnor, Inc.
***Alzo, Inc.

Procedure:

1. Into a clean mixing vessel add the first four ingredients. Bring the Temperature to 45° C. (Part A).
2. In a separate mixing tank make up a solution of sodium hydroxide and half of the water needed, approximately 50% of the water required to make a 50% solution. (Part B)
3. Slowly add part B to part A and continue to heat at 80° C. to effect saponification of the oils. This should take approximately 2 hours.
4. In a third tank make up a solution of ethyl alcohol, sugar and remaining water and Bis-hydroxyethylsoyamine/IPDI Betaine Polymer.
5. Cool A and B down to 50° C. and add D with slow agitation.
6. Fill into molds.

Mild Conditioning Shampoo

Example V

| INGREDIENTS | %, WEIGHT |
|---|---|
| Deionized Water | 58.1 |
| Sodium Laureth Sulfate[1] | 30.0 |
| Lauramide DEA[2] | 3.0 |
| Ricinolylamidododimethylaminopropyl Amine/IPDI Polymer Betaine[2] | 8.0 |
| Methyl Paraben | 0.2 |
| Sodium Chloride | 0.7 |
| Citric Acid, 25%[3] | 0.1 |
| Fragrance, Color pH = 6.9 | q.s. |

[1]Stepan
[2]Alzo, inc.
[3]Pfizer, Inc.

Procedure

1. Into a clean vessel add deionized water. Add the sodium laureth sulfate and heat to 60° C. Add the lauramide DEA and Ricinoloyl-amidodimethyl aminopropyl Amine/IPDI Polymer Betaine.
2. Add the Methyl paraben with citric acid solution and salt to increased viscosity to desired thickness.
3. With agitation, cool the batch down to 35° C. and add the perfume.

Conditioner

Example VI

| INGREDIENTS | %, WEIGHT |
|---|---|
| Deionized Water | 90.9 |
| Cetyldimethylammonium Chloride[1] | 0.6 |
| Ricinoleamidodimethylaminopropyl Amine/IPDI Polymer Betaine[2] | 3.0 |
| Methyl Paraben[2] | 0.1 |
| pH = 6.86 | |

[1]Akzo-Nobel
[2]Alzo, Inc.

Procedure

1. Into a clean vessel, add half of the required water and heat to 65° C. Slowly drop in the Cetyldimethylammonium Chloride along with the Ricinoleamidodimethylaminepropyl Amine/IPDI Polymer Betaine with the Methyl paraben. Stire until the mixture is homogeneous.
2. Add the remaining portion of water and stir until smooth.Cool the batch down to 35° C. and fill.

Temporary Hair Color

Example VII

| INGREDIENTS | %, WEIGHT |
|---|---|
| Deionized Water | 50.0 |
| Bis-(Polyoxyethylene-15) Cocoarnine Amine/IPDI Polymer[1] | 5.0 |
| Tetrasodium EDTA[2] | 0.2 |
| Lanasyn Dark Brown S-GL[3] | 1.0 |
| Lanasyn Navy S-BL[3] | 0.2 |
| Lanasyn Orange S-RL[3] | 0.2 |
| Water (Boiling) | q.s. |
| Lactic Acid, 25%[4] | 0.3 |
| pH = 5.6 | |

[1]Alzo, Inc
[2]Akzo-Nobel
[3]Lowenstein
[4]Purac, Inc.

Procedure

1. Dissolve dyes in boiling water and add to first three ingredients in batch tank.
2. Add Lactic Acid and q.s. with cold water to volume by rinsing out dye container.

Bath and Body Gel

Example VIII

| INGREDIENTS | %, WEIGHT |
|---|---|
| Lauramide DEA* | 2.0 |
| Soyamidopropyl Ethyldimonium Ethosulfate* | 0.5 |
| PEG-150 Distearate* | 1.0 |
| Deionized Water | 53.5 |
| N-Ricinoleamidopropyl-N,N-Dimethyl Amine Oxide/IPDI Copolymer* | 25.0 |
| Cocamidopropylamine Oxide* | 8.0 |

| INGREDIENTS | %, WEIGHT |
|---|---|
| Sodium Laureth (3.0 EO) Sulfate** | 10.0 |
| Preservative | q.s. |
| Fragrance, Color | q.s. |
| | 100.0 |

*Alzo, Inc.
**Stepan

Procedure

1. Weigh Lauramide DEA; heat gently at 50–55° C.
2. Add Soyamidopropyl Ethyldimonium Ethosulfate and PEG-150 Distearate; mix until uniform.
3. With stirring, ad hot water slowly at 40–50° C.
4. Mix until uniform; add Ricinoleamidopropyl Dimethyl Amine Oxide/IPDI Copolymer.
5. Add Sodium Laureth (3.0 EO) Sulfate.
6. Mix thoroughly as viscosity will build.
7. Cool; add preservative, fragrance and color.

Typical Specifications

| Activity | 20% |
|---|---|
| Viscosity* @ 25° C. | 16,000 cps (without fragrance) |
| pH @ 25° C. | 7.0 |

*To increase viscosity, decrease Lauramide DEA
To decrease viscosity, increase Lauramide DEA Clean and Clear Shampoo Example IX

| INGREDIENTS | %, WEIGHT |
|---|---|
| Deionized Water | 53.5 |
| Di-Lauryl Acetyl Dimonium Chloride* | 0.5 |
| Cocamidopropyl Betaine* | 25.0 |
| N-Ricinoleamidopropyl-N,N-Dimethyl Amine Oxide/IPDI Copolymer* | 8.0 |
| Sodium Laureth (3.0 EO) Sulfate** | 10.0 |
| Lauramide DEA* | 3.0 |
| Preservative | q.s. |
| Fragrance | q.s. |

*Alzo, Inc.
**Stepan

Procedure

1. Weigh Lauramide DEA; heat gently at 50–55° C.
2. Add Di-Lauryl Acetyl Dimonium Chloride; mix until uniform.
3. With stirring, add hot water slowly at 40–45° C.
4. Mix until uniform; add Cocamidopropyl Betaine followed by Ricinoleamidopropyl Amine Oxide.
5. Add Sodium Laureth Sulfate.
6. Mix thoroughly, as viscosity will build.
7. Cool; add Preservative and Fragrance.

Typical Specifications

| Activity | 20% |
|---|---|
| Viscosity* @ 25° C. | 3,500 cps (without Fragrance) |
| pH @ 25° C. | 7.0 |

To increase viscosity: Increase Lauramide DEA
To decrease viscosity: Decrease Lauramide DEA Baby Shampoo Example X

| INGREDIENTS | %, WEIGHT |
|---|---|
| Deionized Water | 69.8 |
| Quaternium-15[1] | 0.2 |
| Lauramide DEA[2] | 2.0 |
| PEG-Distearate[2] | 3.0 |
| Cocamidopropyl Betaine[2] | 5.0 |
| R-Ricinoleamidopropyl-N,N-Dimethyl Glycine Dimer with IPDI[2] | 5.0 |
| Lactic Acid[3] | — |
| Fragrance, Color | q.s. |

[1]Dow Chemical
[2]Alzo, Inc.
[3]Purac, Inc.

Procedure

1. Heat water to 45–50° C. With good stirring, add Quaternium-15, Lauramide DEA and PEG-150 DS.
2. When dissolved, add Cocamidopropyl Betaine and Ricinoleamidopropyl Dimethyl Glycine Dimer.
3. Adjust pH if necessary with Lactic Acid. Cool to 30° C.
4. Add Fragrance and Color.

Typical Specification

| Activity, % | 14.0 |
|---|---|
| pH | 5.0 |
| Viscosity* @ 25% | 4000 (Before Fragrance) |

*To increase viscosity, decrease Lauramide DEA
To decrease viscosity, increase Lauramide DEA Shower Gel Shampoo I Example XI

| INGREDIENTS | %, WEIGHT |
|---|---|
| Deionized Water | 46.0 |
| Sodium Lauryl Sulfate[1] | 20.0 |
| Sodium $C_{14}$–$C_{16}$ Olefin Sulfonate[1] | 10.0 |
| Disodium Oleamido PEG-2 Sulfosuccinate[2] | 10.0 |
| Bis-Hydroxyethylsoyamine IPDI Polymer Betaine[2] | 10.0 |
| Cocamidopropylamine Oxide[2] | 3.0 |
| Isostearamidopropyl Ethyl Dimonium Ethosulfate[2] | 1.0 |

| INGREDIENTS | %, WEIGHT |
|---|---|
| Preservative | q.s. |
| Color, Fragrance | q.s. |

[1]Stepan
[2]Alzo, Inc.

Procedure

1. Heat Water to 60° C. With stirring, add Isostearamidopropyl Ethyl Dimonium Ethosulfate.

2. Add Bis-Hydroxyethylsoyamine IPDI Polymer Betaine.

3. Add Cocamidopropylamine Oxide and Disodium Oleamido PEG-2 Sulfosuccinate.

4. Slowly add Sodium $C_{14}$–$C_{16}$ Olefin Sulfonate.

5. Increase stirring and slowly add Sodium Lauryl Sulfate. Mix thoroughly at high rpm until uniform.

6. To clear bubble formation, heat finished product in an oven @45° to 50° C. overnight.

Typical Specifications

| | |
|---|---|
| Activity | 20% |
| Viscosity @ 25° C. | 17,000 cps (without Fragrance) |
| pH @ 25° C. | 6.8 |

Shower Gel Shampoo II

Example XII

| INGREDIENTS | %, WEIGHT |
|---|---|
| Deionized Water | 46.0 |
| Sodium Lauryl Sulfate[1] | 20.0 |
| Sodium $C_{14}$–$C_{16}$ Sulfonate[1] | 10.0 |
| Disodium Oleamido PEG-2 Sulfosuccinate[2] | 10.0 |
| R-Ricinoleamidopropyl-N,N-Dimethyl Glycine Dimer with IPDI[2] | 10.0 |
| N-Ricinoleamido Propyl-N,N-Dimethyl Amine Oxide/IPDI Copolymer[2] | 3.0 |
| Isosteararmidopropyl Ethyl Dimonium Ethosulfate[2] | 1.0 |
| Preservative | q.s. |
| Color, Fragrance | q.s. |

[1]Stepan
[2]Alzo, Inc.

Procedure

1. Heat Water to 60° C. With stirring, add Isostearamidopropyl Ethyl Dimonium Ethosulfate.

2. Add R-Ricinoleamidopropyl-N,N-Dimethyl Glycine Dimer with IPDI.

3. Add N-Ricinoleamido Propyl-N,N-Dimethyl Amine Oxide/IPDI Copolymer.

4. Slowly add Sodium $C_{14-16}$ Olefin Sulfonate.

5. Increase stirring and slowly add Sodium Lauryl Sulfate. Mix thoroughly at high rpm until uniform.

6. To clear bubble formation, heat finished product in an oven at 45° C. to 50° C. overnight.

Typical Specifications

| | |
|---|---|
| Activity | 20 |
| Viscosity @ 25° C. | 17,000 cps (without Fragrance) |
| pH @ 25° C. | 6.8 |

Shower Gel Shampoo

Example XIII

| INGREDIENTS | %, WEIGHT |
|---|---|
| Sodium Lauryl Sulfate[1] | 20.0 |
| Sodium $C_{14}$–$C_{16}$ Olefin Sulfonate[1] | 10.0 |
| Disodium Oleamido PEG-2 Sulfosuccinate[2] | 10.0 |
| R-Ricinoleamidopropyl-N,N-Dimethyl Glycine Dimer with IPDI[2] | 10.0 |
| N-Ricinolieamido Propyl-N,N-Dimethyl Amine Oxide/IPDI Copolymer[2] | 3.0 |
| Isostearainidopropyl Ethyl Dimonium Ethosulfate[2] | 1.0 |
| Preservative | q.s. |
| Color, Fragrance | q.s. |
| Deionized Water | q.s. - 100 |

[1]Stepan
[2]Alzo, Inc.

Procedure

1. Heat water to 50° C. With stirring, add Isostearamidopropyl Ethyl Dimonium Ethosulfate.

2. Add R-Ricinoleamidopropyl-N,N-Dimethyl Glycine Dimer with IPDI.

3. Add N-Ricinoleamidopropyl-N,N-Dimethyl Amine Oxide/IPDI Copolymer

4. Slowly add Sodium $C_{14}$–$C_{16}$ Olefin Sulfonate and Disodium Olamido PEG-2 Sulfosuccinate.

5. Increase stirring and slowly add Sodium Lauryl Sulfate. Mix thoroughly.

6. To clear bubble formation, heat finished product in an oven at 45–50° C. overnight.

Typical Specifications

| | |
|---|---|
| Activity | 20% |
| Viscosity @ 25° C. | 16,000 cps (without Fragrance) |
| pH @ 25° C. | 6.8 |

Hair Conditioner—Oil Free

Example XIV

| INGREDIENTS | %, WEIGHT |
|---|---|
| Behenamidopropyl Dimethylamine Behenate* | 1.3 |
| N-Ricinoleamidopropyl-N,N-Dimethyl Amine Oxide/IPDI Copolymer* | 1.4 |
| Cetyl Alcohol* | 1.1 |
| Glycerol Stearate* | 1.0 |
| Isosteareth-2 Phosphate* | 1.3 |
| Propylene Glycol** | 1.3 |

-continued

| INGREDIENTS | %, WEIGHT |
| --- | --- |
| Deionized Water | 92.6 |
| Fragrance | q.s. |
| Color | q.s. |

*Alzo, Inc.
**Union Carbide, Inc.

Procedure

1. Weigh Propylene Glycol into a beaker; heat to 70–75° C. with stirring. Add Behenamidopropyl Dimethylamine Behenate, N-Ricinoleamidopropyl-N,N-Dimethyl Amine Oxide/IPDI Copolymer and Glycerol Stearate and Cetyl Alcohol. Mix until dissolved while maintaining temperature.

2. Add Isosteareth-2 Phosphate.

3. With good mixing, add Water very slowly to oil phase.

4. Maintain temperature at 70–75° C.; mix until uniform

5. Cool to 40° C.; add Fragrance and Color.

Typical Specifications

| Activity, % | 7.4 |
| --- | --- |
| Appearance @ 25° C. | White Lotion |
| pH | 5.5 (Typical) |

Hair Conditioner—Concentrate

Example XV

| INGREDIENTS | %, WEIGHT |
| --- | --- |
| Beheneamidopropyl Dimethylamine Behenate* | 13.5 |
| Stearamidopropyl Dimethylamine * | 4.5 |
| Cetyl Alcohol* | 2.6 |
| Glycerol Stearate* | 1.8 |
| Isosteareth-2 Phosphate* | 2.5 |
| Propylene Glycol** | 18.0 |
| PEG-2-Soyamine IPDI Betaine* | 2.0 |
| Deionized Water | 55.1 |
| Fragrance | q.s. |
| Color | q.s. |

*Alzo, Inc.
**Union Carbide

Procedure

1. Weigh Propylene Glycol into a beaker; heat to 70–75° C. with stirring. Add Beheneamidopropyl Dimethylamine Behenate, Stearamidopropyl Dimethylamine, Glycerol Stearate and Cetyl Alcohol. Mix until dissolved while maintaining temperature.

2. Add Isosteareth-2 Phosphate.

3. With good mixing, add water very to Steps 1 and 2.

4. Maintain temperature @70–75° C.; mix until uniform.

5. Cool to 40° C.; add Fragrance and Color.

Typical Specifications

| Activity, % | 44 |
| --- | --- |
| Apperance @ 25° C. | Cream Soft Paste |
| pH 1.0% = | 6 (Typical) |

Conditioning Shampoo #1 (Pearlescent)

Example XVI

| INGREDIENTS | %, WEIGHT |
| --- | --- |
| Deionized Water | 46.8 |
| Quaternium-15[1] | 0.2 |
| Soyamidopropyl Ethyldimonium Ethosulfate[2] | 1.5 |
| Glycereth-7 Hydroxystearate Copolymer[2] | 1.0 |
| Glycol Stearate[2] | 0.5 |
| Cocamidopropyl Betaine[2] | 10.0 |
| R-Ricinoleamidopropyl-N,N-Dimethyl Glycine Dimer with IPDI[2] | 10.0 |
| Sodium Alpha Olefin Sulfonate[3] | 10.0 |
| Sodium Lauryl Sulfate[3] | 20.0 |
| Color | q.s. |
| Fragrance | q.s. |

[1]Dow Chemical Co.
[2]Alzo, Inc.
[3]Stepan

Procedure

1. Heat water to 50–60° C. With fast stirring, slowly add Quaternium-15 and Soyamidopropyl Ethyldimonium Ethosulfate. Mix to dissolve.

2. Add Glycereth-7 Hydroxystearate Copolymer and Glycol Stearate. Mix to dissolve.

3. With fast mixing, slowly add Cocoamidopropyl Betaine, Sodium Alpha Olefin Sulfonate and Sodium Lauryl Sulfate.

4. When uniform, cool; add Color and Fragrance.

Typical Specification

| Activity, % | 22 |
| --- | --- |
| Viscosity | 3,000 cps (Without Fragrance) |
| pH @ 25° C. | 7.0 |

Liquid Hand Soap—Pearlescent

Example XVII

| INGREDIENTS | %, WEIGHT |
| --- | --- |
| Deionized Water | 51.8 |
| Quaternium-15[1] | 0.2 |
| Isostearamidopropyl Ethyldimonium Ethosulfate[2] | 1.0 |
| R-Ricinoleamidopropyl-N,N-Dimethyl Glycine Dimer with IPDI[2] | 10.0 |
| Lauramide DEA[2] | 1.0 |
| Glycol Stearate[2] | 1.0 |
| Sodium Lauryl Sulfate[3] | 35.0 |

| INGREDIENTS | %, WEIGHT |
|---|---|
| Preservative | q.s. |
| Fragrance | q.s. |

[1]Dow Chemical Co.
[2]Alzo, Inc.
[3]Stepan

Procedure

1. Heat water to 45–50° C. With stirring, add Quaternium-15 and Isostearamidopropyl Ethyldimonium Ethosulfate. Mix to dissolve.

2. Add R-Ricinoleaidopropyl-N,N-Dimethyl Glycine Dimer with IPDI.

3. Dissolve (melt) Glycol Stearate in Lauramide DEA, then add to above.

4. Add Sodium Lauryl Sulfate.

5. When uniform, cool and add Preservative and Fragrance.

Typical Specification

| Activity, % | 18 |
|---|---|
| Viscosity @ 25° C. | 4,000–6,000 (Without Fragrance) |
| pH @ 25° C. | 8.0 |

Natural Conditioning Shampoo

Example XVIII

| INGREDIENTS | % WEIGHT | INCI NAME |
|---|---|---|
| Water (Deionized) | 48.5 | |
| Polyderm PPI-SA-15* | 1.5 | Proposed: PEG-15 Soyanim/ IPDI Copolymer |
| Foamtaine CAB-G (45%)* | 22.0 | Cocamidopropyl Betaine |
| Foatntaine PPI-SA-15* | 5.0 | N/A |
| Foamox PPI-SA-15* | 3.0 | N/A |
| Sodium Lauryl Ether | 20.0 | Sodium Laureth (3.0) Sulfate |
| Preservative | q.s. | |
| Fragrance | q.s. | |

*From Alzo, Inc. Sayreville, New Jersey

Procedure

1. Heat water to 45° C. With stirring, add Foamquat PPI-SA-15 to dissolve.

2. Add Foamtaine CAB-IG.

3. Add Foamtaine PPI-SA-15 and Foamox PPI-SA-15.

4. Slowly add Sodium Lauryl Ether Sulfate; mix thoroughly, as viscosity will build rapidly.

5. Cool, q.s. with Preservative and Fragrance.

Typical Specifications

| Activity: | 20% |
|---|---|
| Viscosity: | 2800 cps (Without Fragrance) |
| pH @ 25° C.: | 4.9 |

Natural Mild Conditioning Shampoo

Example IXX

| INGREDIENTS | % WEIGHT | INCI NAME |
|---|---|---|
| Water (Deionized) | 48.5 | |
| Polyderm PPI-SA-15* | 0.5 | Proposed: PEG-15 Soyamine/ IPDI Copolymer |
| Foamtaine CAB-G (45%)* | 22.0 | Cocamidopropyl Betaine |
| Foamtaine PPI-SA-15* | 6.0 | N/A |
| Sodium Lauryl Ether Sulfate (30%) | 20.0 | Sodium Laureth (3.0 EO) Sulfate |
| Foamid SLM* | 3.0 | Lauramide-MyristamideDEA |
| Preservative | q.s. | |
| Fragrance | q.s. | |

Procedure

1. Heat water to 45° C. With stirring, add Polyderm PPI-SA-15 to dissolve.

2. Add Foamtaine CAB-G, followed by Foamtaine PPI-SA-15.

3. Add Sodium Lauryl Ether Sulfate.

4. Add Foamid SLM; mix thoroughly, as viscosity will build.

5. Cool, q.s. with Preservative and Fragrance.

Typical Specifications

| Activity: | 20% |
|---|---|
| Viscosity @ 250 C: | 2900 cps (Without Fragrance) |
| pH @ 25*C: | 5.5 |

*From Alzo, Inc.

Shower Gel Shampoo

EXAMPLE XX

| INGREDIENTS | % WEIGHT | INCI NAME |
|---|---|---|
| Water (Deionized) | 46.0 | |
| Foamquat PPI-SA-15* | 1.0 | N/A |
| Foamtaine CAB-G (45%)* | 10.0 | Cocamidopropyl Betaine |
| Foamtaine PPI-SA-15* | 5.0 | N/A |
| Foamox PPI-SA-15* | 3.0 | N/A |
| Alpha Olefin Sulfonate (40%) | 15.0 | Sodium $C_{14}$—$C_{16}$ Olefin Sulfonate |
| Sodium Lauryl Sulfate (30%) | 20.0 | Sodium Lauryl Sulfate |
| Preservative | q.s. | |
| Color, Fragrance | q.s. | |

*ALZO INC., Sayreville, New Jersey

Procedure

1. Heat water to 50° C. With stirring, add Foamquat PPI-SA-15 to dissolve.

2. Add Foamtaine CAB-G and Foamtaine PPI-SA-15.

3. Add Foamox PPI-SA-15.

4. Slowly add Alpha Olefin Sulfonate; viscosity builds slightly.

5. Increase stirring and slowly add Sodium Lauryl Sulfate. Mix thoroughly.

6. To clear up bubble formation, heat finished product in an oven at 45° C.–50° C. overnight.

Typical Specifications

| | |
|---|---|
| Activity: | 20% |
| Viscosity: | 16,000 cps (Without Fragrance) |
| pH @ 25° C. | 6.8 |

Liquid Hand Soap (Pearlescent)

Example XXI

| INGREDIENTS | % WEIGHT | INCI NAME |
|---|---|---|
| Water (Deionized) | 51.8 | |
| Dowicil-200[1] | 0.2 | Quaternium-15 |
| Polyderm PPI-SAD-15 | 1.0 | N/A |
| Foamtaine CAB-G (45%)[2] | 10.0 | Cocamidopropyl Betaine |
| Foamid SLM[2] | 1.0 | Lauramide DEA |
| Dermol EGMS[2] | 1.0 | Glycol Stearate |
| Stepanol WA Paste (30%)[3] | 35.0 | Sodium Lauryl Sulfate |
| Preservative | q.s. | |
| Fragrance | q.s. | |

[1]Dow Chemical
[2]Alzo Inc.
[3]Stepan

Procedure

1. Heat water to 45° C.–50° C. With stirring, add Dowicil-200 and Polyderm PPI-SAD-15. Mix to dissolve.

2. Add Foatntaine CAB-G.

3. Dissolve (melt) Dermol EGMS in Foamid SLM, then add to above.

4. Add Stepanol WA Paste.

5. When uniform, cool and add Preservative and Fragrance.

Typical Specifications

| | |
|---|---|
| Activity: | 18% |
| Viscosity @ 25° C. | 4,000–6,000 (Without Fragrance) |
| pH @ 25° C. | 8.0 |

*To increase viscosity, decrease % amide. To decrease viscosity, increase % amide.

Polymeric Conditioning Shampoo (Pearlescent)

Example XXII

| INGREDIENTS | % WEIGHT | INCI NAME |
|---|---|---|
| Water (Deionized) | 46.8 | |
| Dowicil-200[1] | 0.2 | Quaternium-15 |
| Foamquat SOAS[2] | 1.5 | Soyamidopropyl Ethyl dimonium Ethosulfate |
| Polyderm PPI-SA-15[2] | 1.0 | Proposed: PEG-15 Soyamine/ 1PDI Copolymer |
| Dermowax EGMS[2] | 0.5 | Glycol Stearate |
| Foamtaine CAB-G (45%)[2] | 20.0 | Cocamidopropyl Betaine |
| Bio-Terge AS (40%)[3] | 10.0 | Sodium Alpha Olefin Sulfonate |
| Stepanol WA Paste (30%)[3] | 20.0 | Sodium Lauryl Sulfate |
| Color | q.s. | |
| Fragrance | q.s. | |

[1]Dow Chemical
[2]Alzo Inc.
[3]Stepan

Procedure

1. Heat water to 55° C.–60° C. With fast stirring, slowly add Dowicil-200 and Foamquat SOAS. Mix to dissolve.

2. Add Polyderm PPI-SA-15 and EGMS. Mix to dissolve.

3. With fast mixing, slowly add Foamtaine CAB-G, Alpha Olefin and Sodium Lauryl Sulfate.

4. When uniform, cool; add Color and Fragrance.

Typical Specifications

| | |
|---|---|
| Activity: | 22% |
| Viscosity: | 3,000 (Without Fragrance) |
| pH @ 25° C.: | 7.0 |

Natural Conditioning Shampoo

Example XXIII

| INGREDIENTS | % WEIGHT | INCI NAME |
|---|---|---|
| Water (Deionized) | 48.5 | |
| Polyderm PPI-SA* | 1.5 | Proposed: PEG-2 Soyamine/ IPDI Copolymer |
| Foamtaine CAB-G (45%)* | 22.0 | Cocamidopropyl Betaine |
| Foamtaine PPI-SA* | 5.0 | N/A |
| Foamox PPI-SA* | 3.0 | N/A |
| Sodium Lauryl Ether | 20.0 | Sodium Laureth (3.0) Sulfate |
| Preservative | q.s. | |
| Fragrance | q.s. | |

*Alzo, Inc., Sayreville, New Jersey

Procedure

1. Heat water to 45° C. With stirring, add Foamquat PPI-SA to dissolve.

2. Add Foamtaine CA-B-G.

3. Add Foamtaine PPI-SA and Foamox PPI-SA.

4. Slowly add Sodium Lauryl Ether Sulfate; mix thoroughly, as viscosity will build rapidly.

5. Cool, q.s. with Preservative and Fragrance.

Typical Specifications

| | |
|---|---|
| Activity: | 20% |
| Viscosity: | 2800 cps (Without Fragrance) |
| pH @ 25° C.: | 4.9 |

Natural Mild Conditioning Shampoo

Example XIV

| INGREDIENTS | WEIGHT | INCI NAME |
|---|---|---|
| Water (Deionized) | 48.5 | |
| Polyderm PPI-SA* | 0.5 | Proposed: PEG-2 Soyamine/IPD1 Copolymer |
| Foamtaine CAB-G (45%)* | 22.0 | Cocamidopropyl Betaine |
| Foamtaine PPI-SA* | 6.0 | N/A |
| Sodium Lauryl Ether Sulfate (30%) | 20.0 | Sodium Laureth (3.0 EO) Sulfate |
| Foamid SLM* | 3.0 | Lauramide-MyristamideDEA |
| Preservative | q.s. | |
| Fragrance | q.s. | |

*Alzo, Inc., Sayreville, New Jersey

Procedure

1. Heat water to 45° C. With stirring, add Polyderm PPI-SA to dissolve.
2. Add Foamtaine CAB-G, followed by Foamtaine PPI-SA.
3. Add Sodium Lauryl Ether Sulfate.
4. Add Foamid SLM; mix thoroughly, as viscosity will build.
5. Cool, q.s. with Preservative and Fragrance.

Typical Specifications

| | |
|---|---|
| Activity: | 20% |
| Viscosity @ 25° C.: | 2900 cps (Without Fragrance) |
| pH @ 25° C.: 5.5 | |

Shower Gel Shampoo

Example XXV

| INGREDIENTS | WEIGHT | INCI NAME |
|---|---|---|
| Water (Dionized) | 46.0 | |
| Foamquat PPI-SA* | 1.0 | N/A |
| Foamtaine CAB-G (45%)* | | 10.0 Cocamidopropyl Betaine |
| Foamtaine PPI-SA* | 5.0 | N/A |
| Foamox PPI-SA* | 3.0 | N/A |
| Alpha Olefin Sulfonate (40%) | | 15.0 Sodium $C_{14}$-$C_{16}$ Olefin Sulfonate |
| Sodium Lauryl Sulfate (30%) | | 20.0 Sodium Lauryl Sulfate |
| Preservative | q.s. | |
| Color, Fragrance | q.s. | |

*Alzo, Inc., Sayreville, New Jersey

Procedure

1. Heat water to 50° C. With stirring, add Foamquat PPI-SA to dissolve.
2. Add Foamtaine CAB-G and Foamtaine PPI-SA.
3. Add Foamox PPI-SA.
4. Slowly add Alpha Olefin Sulfonate; viscosity builds slightly.
5. Increase stirring and slowly add Sodium Lauryl Sulfate. Mix thoroughly.
6. To clear up bubble formation, heat finished product in an oven at 50C-500C overnight.

Typical Specifications

| | |
|---|---|
| Activity: | 20% |
| Viscosity: | 16,000 cps (Without Fragrance) |
| pH @ 250 C.: | 6.8 |

Liquid Hand Soap (Pearlescent)

Example XXVI

| INGREDIENTS | WEIGHT | INCI NAME |
|---|---|---|
| Water Deionized | 51.8 | |
| Dowicil-200[1] | 0.2 | Quaternium-15 |
| Polyderm PPI-SAD[2] | 1.0 | N/A |
| Foamtaine CAB-G (45%)[2] | 10.0 | Cocamidopropyl Betaine |
| Foamid SLM[2] | 1.0 | Lauramide DEA |
| Dermol EGMS[2] | 1.0 | Glycol Stearate |
| Stepanol WA Paste (30%)[3] | 35.0 | Sodium Lauryl Sulfate |
| Preservative | q.s. | |
| Fragrance | q.s. | |

[1]Dow Chemical
[2]Alzo Inc.
[3]Stepan

Procedure

1. Heat water to 45° C.–50° C. With stirring, add Dowicil-200 and Polyderm PPI-SAD. Mix to dissolve.
2. Add Foamtaine CAB-G.
3. Dissolve (meft) Dermol EGMS in Foamid SLM, then add to above.
4. Add Stepanol WA Paste.
5. When uniform, cool and add Preservative and Fragrance.

Typical Specifications

| | |
|---|---|
| Activity: | 18% |
| Viscosity (P 250 C.: | 4,000–6,000 (Without Fragrance) |
| pH @ 25° C.: | 8.0 |

*To increase viscosity, decrease % amide. To decrease viscosity, increase % amide.

Polymeric Conditioning Shampoo

Example XXVII

| INGREDIENTS | WEIGHT | INCI NAME |
|---|---|---|
| Water (Deionized) | 46.8 | |
| Dowicil-200[1] | 0.2 | Quaternium-15 |
| Foamquat SOAS[2] | 1.5 | Soyamidopropyl Ethyl dimonium Ethosulfate |
| Polyderm PPI-SA[2] | 1.0 | Proposed: PEG-2 Soyamine/IPDI Copoymer |
| Dermowax EGMS[2] | 0.5 | Glycol Stearate |
| Foamtaine CAB-G (45%)[2] | 20.0 | Cocamidopropyl Betaine |
| Bio-Terge AS (40%)[3] | 10.0 | Sodium Alpha Olefin Sulfonate |

-continued

| INGREDIENTS | WEIGHT | INCI NAME |
|---|---|---|
| Stepanol WA Paste (30%)[3] | 20.0 | Sodium Lauryl Sulfate |
| Color | q.s. | |
| Fragrance | q.s. | |

[1]Dow Chemical
[2]Alzo Inc.
[3]Stepan

Procedure

1. Heat water to 55° C.–60° C. With fast stirring, slowly add Dowicil-200 and Foamquat SOAS. Mix to dissolve.

2. Add Polyderm PPI-SA and EGMS. Mix to dissolve.

3. With fast mixing, slowly add Foamtaine CAB-G, Alpha Olefin and Sodium Lauryl Sulfate.

4. When uniform, cool; add Color and Fragrance.

Typical Specifications

| Activity: | 22% |
|---|---|
| Viscosity: | 3,000 (Without Fragrance) |
| pH @ 250 C.: | 7.0 |

Natural Conditioning Shampoo

Example XVIII

| INGREDIENTS | % WEIGHT | INCI NAME |
|---|---|---|
| Water (Deionized) | 48.5 | |
| Polyderm PPI-RC | 1.5 | N/A |
| Foamtaine CAB-G (45%)* | 22.0 | Cocamidopropyl Betaine |
| Foamtaine PPI-RC* | 5.0 | N/A |
| Foamox PPI-RC* | 3.0 | N/A |
| Sodium Lauryl Ether | 20.0 | Sodium Laureth (3.0) Sulfate |
| Preservative | q.s. | |
| Fragrance | q.s. | |

*Alzo, Inc., Sayreville, New Jersey

Procedure

1. Heat water to 45° C. With stirring, add Foamquat PPI-RC to dissolve.

2. Add Foamtaine CAB-G.

3. Add Foamtaine PPI-RC and Foamox PPI-RC.

4. Slowly add Sodium Lauryl Ether Sulfate; mix thoroughly, as viscosity will build rapidly.

5. Cool, q.s. with Preservative and Fragrance.

Typical Specifications

| Activity: | 20% |
|---|---|
| Viscosity: | 2800 cps (Without Fragrance) |
| pH @ 250 C.: | 4.9 |

Natural Mild Conditioning Shampoo

Example XXIX

| INGREDIENTS | WEIGHT | INCI NAME |
|---|---|---|
| Water (Deionized) | 48.5 | |
| Polyderm PPI-RC* | 0.5 | N/A |
| Foamtaine CAB-G (45%)* | 22.0 | Cocamidopropyl Betaine |
| Foamtaine PPI-RC* | 6.0 | N/A |
| Sodium Lauryl Ether Sulfate (30%) | 20.0 | Sodium Laureth (3.0 EO) Sulfate |
| Foamid SLM* | 3.0 | Lauramide-Myristamide DEA |
| Preservative | q.s. | |
| Fragrance | q.s. | |

*Alzo, Inc. Sayreville, New Jersey

Procedure

1. Heat water to 45° C. With stirring, add Polyderm PPI-RC to dissolve.

2. Add Foamtaine CAB-G, followed by Foamtaine PPI-RC.

3. Add Sodium Lauryl Ether Sulfate.

4. Add Foamid SLM; mLx thoroughly, as viscosity will build.

5. Cool, q.s. with Preservative and Fragrance.

Typical Specifications

| Activity: | 20% |
|---|---|
| Viscosity (& 25° C.: | 2900 cps (Without Fragrance) |
| pH @ 250 C.: | 5.5 |

Shower Gel Shampoo

Example XXX

| INGREDIENTS | WEIGHT | INCI NAME |
|---|---|---|
| Water (Deionized) | 46.0 | |
| Foamquat PPI-RC* | 1.0 | N/A |
| Foamtaine CAB-G (45%)* | 10.0 | Cocamidopropyl Betaine |
| Foamtaine PPI-RC* | 5.0 | N/A |
| Foairnox PPI-RC* | 3.0 | N/A |
| Alpha Olefin Sulfonate (40%) | 15.0 | Sodium $C_{14}$–$C_{16}$ Olefin Sulfonate |
| Sodium Lauryl Sulfate (30%) | 20.0 | Sodium Lauryl Sulfate |
| Preservative | q.s. | |
| Color, Fragrance | q.s. | |

*Alzo, Inc. Sayreville, New Jersey

Procedure

1. Heat water to 50° C. With stirring add Foamquat PPI-RC to dissolve.

2. Add Foamtaine CAB-G and Foamtaine PPI-RC.

3. Add Foamox PPI-RC.

4. Slowly add Alpha Olefin Sulfonate; viscosity builds slightly.

5. Increase stirring and slowly add Sodium Lauryl Sulfate. Mix thoroughly.

6. To clear up bubble formation, heat finished product in an oven at 45° C.–50° C. overnight.

Typical Specifications

| | |
|---|---|
| Activity: | 20% |
| Viscosity: | 16,000 cps (Without Fragrance) |
| pH @ 25° C.: | 6.8 |

Liquid Hand Soap (Pearlescent)

Example XXXI

| INGREDIENTS | WEIGHT | INCI NAME |
|---|---|---|
| Water (Deionized) | 51.8 | |
| Dowicil-200[1] | 0.2 | Quaternium-15 |
| Polyderm PPI-RCD[2] | 1.0 | N/A |
| Foamtaine CAB-G (45%)[2] | 10.0 | Cocamidopropyl Betaine |
| Foamid SLM[2] | 1.0 | Lauramide DEA |
| Dermol EGMS[2] | 1.0 | Glycol Stearate |
| Stepanol WA Paste (30%)[3] | 35.0 | Sodium Lauryl Sulfate |
| Preservative | q.s. | |
| Fragrance | q.s. | |

[1]Dow Chemical
[2]Alzo Inc.
[3]Stepan

Procedure

1. Heat water to 45° C.–50° C. With stirring, add Dowicil-200 and Polyderm PPI-RCD. Mix to dissolve.

2. Add Foamtaine CAB-G.

3. Dissolve (melt) Dermol EGM in Foamid SLM, then add to above.

4. Add Stepanol WA Paste.

5. When uniform, cool and add Preservative and Fragrance.

Typical Specifications

| | |
|---|---|
| Activity: | 18% |
| Viscosity @ 25° C. | 4,000–6,000 (Without Fragrance) |
| pH @ 25° C.: | 8.0 |

*To increase viscosity, decrease % amide. To decrease viscosity, increase % amide.

Polymeric Conditioning Shampoo (Pearlescent)

Example XXXII

| INGREDIENTS | WEIGHT | INCI NAME |
|---|---|---|
| Water (Deionized) | 46.8 | |
| Dowicil-200[1] | 0.2 | Quaternium |
| Foamquat SOAS[2] | 1.5 | Soyamidopropyl Ethyldimonium Ethosulfate |
| Polyderm. PPI-RC[2] | 1.0 | N/A |
| Dermowax EGMS[2] | 0.5 | Glycol Stearate |
| Foamtaine CAB-G (45%)[2] | 20.0 | Cocamidopropyl Betaine |
| Bio-Terge AS (40%)[3] | 10.0 | Sodium Alpha OlefinSulfonate |

-continued

| INGREDIENTS | WEIGHT | INCI NAME |
|---|---|---|
| Stepanol WA Paste (30%)[3] | 20.0 | Sodium Lauryl Sulfate |
| Color | q.s. | |
| Fragrance | q.s | |

[1]Dow Chemical
[2]Alzo Inc.
[3]Stepan

Procedure

1. Heat water to 55OC-60OC. With fast stirring, slowly add Dowicil-200 and Foamquat SOAS. Mix to dissolve.

2. Add Polyderm PPI-RC and EGMS. Mix to dissolve.

3. With fast mixing, slowly add Foamtaine CAB-G, Alpha Olefin and Sodium Lauryl Sulfate.

4. When uniform, cool; add Color and Fragrance.

Typical Specification

| | |
|---|---|
| Activity: | 22% |
| Viscosity: | 3,000 (Without Fragrance) |
| pH @ 25° C.: | 7.0 |

Irritation Studies

Eye Irritation Study of Polyderm PPI-SA/Di-PEG-2 Soyamine IPDI Copolymer

Six normal healthy albino rabbits were used for this study. On the day of the study prior to testing, each animal had their eyes examined for irritation or corneal damage; any animal exhibiting abnormalities was excluded from testing.

Each animal had 0.1 ml of the test material (Polyderm PPI-SA/Di-PEG-2 Soyamine IPDI Copolymer in 1.0% Sunflower Oil) instilled into the conjuctival sac of the test eye. The contralater untreated eye served as a control for that animal.

The treated and untreated eyese were examined and graded at 24, 48 and 72 hours post instillation.

A test is interpreted as positive in this test if four or more animals exhibit a positive response on the cornea, iris or conjunctiva. A test is interpreted as negative if one or less animals exhibit a positive response of the cornea, iris or conjunctiva. A test is considered inconclusive if two or three animals exhibit a positive response on the cornea, iris or conjunctiva. The test may be repeated with a different group of six animals and is positive if three or more animals no exhibit a positive response.

The submitted material, Polyderm PPI-SA/Di-PEG-2 Soyamine/IPDI Copolymer in 1.0% Sunflower Oil produced minimal conjunctival irritation in six of six animals tested. All signs of irritation cleared by day 3 of the study. Consequently, the material was not considered a primary eye irritant.

Dermal Irritation Study of Foa,taome PPI-RC RicinoleamidopropylDimenthol Glycine Dimer w/IPDI The test was designed to identify substances which are primary irritants to rabbit skin.

Method of Assay

Three New Zealand white rabbits, about three months of age, weighing approximately 2–3 kilograms, were obtained from a USDA licensed dealer. The animals were checked upon receipt for diarrhea and dehydration, respiratory difficultires, postural deficiencies, and general conditions of health.

Animals were acclimated for at least four days prior to initiation of the study. They were housed in clean cages, in a temperature controlled environment with a twelve hour light/dark cycle. Diet consisted of a growth and maintenance ration obtained from a commercial producer, and water, ad libitum. Each animal was identified by an individual eartag number on the right ear, as well as a corresponding cage card.

Twenty-four hours prior to test initiation, the animals were reexamined and any found in poor condition, particularly those with skin eruptions or dermal lesions, were not used. Animals were prepared for testing by close-clipping the skin of the mid-dorsal area of the trunk, between the scapulae and the pelvis, using a small animal clipper equipped with a #40 (surgical) blade.

Four test sites, each 2.5 cm square, were chosen on opposite sides of the vertebral column. The left side of the animal is maintained intact and the test sites on the right is further prepared by abrading with a sterile 21 gauge hypodermic needle. The abrasions are longitudinal epidermal incisions, sufficiently deep to penetrate the stratum corneum, but not so deep as to destroy the integrity of the derma.

A single application of 0.5 ml. of test material was made on each anterior test site and each site was then covered with a one-inch square gauze patch.

After both test sites were treated, the entire trunk of each animal was encased in an impermeable occlusive wrappng held in place with Elastikon tape. This aided in maintaining the test material and patches in position and prevents the evaporation of any possible volatile components in the material.

The wrapping and test article were removed 24 hours following application; any remaining test material was gently wiped from the skin. Each test site was individiually examined an and scored at twenty-four and seventy-two hours post dosing for erythema and edema using the Draize skin scoring scale. The presence of effects not listed in the scoring scale was also noted.

Interpretation of Assay

Following the seventy-two hour reading, the scores for twenty-four and seventy-two hour gradings were averaged to determine the primary irritation index. A score of 5.0 or more indicates a primary dermal irritant.

Summary

The test material, under occluded test conditions, produced very slight to well-defined erythema and very slight edema. The primary irritation score was 2.01. This is consistent with being classified as a non-skin irritant.

It is to be understood by those skilled in the art that the foregoing description and examples are merely illustrative of the present invention, and should in no way be intrepreted as limiting the scope of the present invention. Variations of the detail presented herein may be made without departing from the spirit and scope of the present invention as defined by the following claims.

What is claimed is:

1. A compound according to the structure:

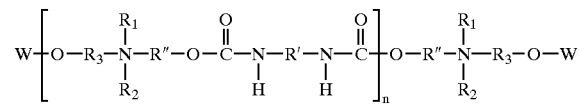

where R' is a $C_6$ through $C_{36}$ linear, cyclic or branch-chained saturated or unsaturated hydrocarbon group which is substituted or unsubstituted, monomeric or dimeric, a phenyl or benzyl group or substituted phenyl or benzyl group, an alkylphenyl, alkylbenzyl or substituted alkylphenyl or alkylbenzyl group;

R" is selected from a $C_1$ through $C_{36}$ linear, branch-chained or cyclic saturated or unsaturated hydrocarbon group which is substituted or unsubstituted, monomeric or dimeric, a phenyl or benzyl group or substituted phenyl or benzyl group, an alkylphenyl, alkylbenzyl, substituted alkylphenyl or alkylbenzyl group, a

group or a

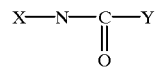

group;

R'" is a $C_1$ through $C_{36}$ linear or branch-chained, cyclic, saturated or unsaturated hydrocarbon group which is substituted or unsubstituted, monomeric or dimeric or a phenyl group, benzyl group or substituted phenyl or benzyl group, an alkylphenyl, alkylbenzyl, substituted alkylphenyl or alkylbenzyl group; and $R_1$ is a $C_1$ through $C_{36}$ linear or branch-chained saturated or unsaturated hydrocarbon group which is substituted or unsubstituted, an aromatic group, including a phenyl or benzyl group or substituted phenyl or benzyl group, an alkylphenyl, alkylbenzyl or substituted alkylphenyl or alkylbenzyl group;

$R_2$ is a free electron pair, O, a hydrogen or a quaternium group, or a mixture of hydrogen and quaternium groups, with the proviso that when $R_2$ is H and/or a quaternium group, the nitrogen to which said hydrogen or quaternium group is bonded is positively charged and forms a salt with a negatively charged counterion T;

$R_3$ is a $C_1$ through $C_{36}$ linear or branch-chained saturated or unsaturated hydrocarbon group which is substituted or unsubstituted, an aromatic group including a phenyl or benzyl group or substituted phenyl or benzyl group, an alkylphenyl, alkylbenzyl or substituted alkylphenyl or alkylbenzyl group;

each of X and Y is independently a $C_1$ through $C_{36}$ linear, cyclic or branch-chained saturated or unsaturated hydrocarbon group which is substituted or unsubstituted, a phenyl or benzyl group or a substituted phenyl or benzyl group, an alkylphenyl, alkylbenzyl or substituted alkylphenyl or alkylbenzyl group;

W is a sulfosuccinate group or a $C_4$-$C_{10}$ alkyl sulfonate group, a phosphate group

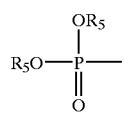

or a

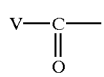

group where V is a $C_1$ through $C_{10}$ linear, cyclic or branch-chained saturated or unsaturated hydrocarbon group which is substituted or unsubstituted, a phenyl or benzyl group or substituted phenyl or benzyl group, an alkylphenyl, alkylbenzyl or substituted alkylphenyl or alkylbenzyl group and $R_5$ is a $C_1$ to $C_6$ alkyl group or a metal cation selected from the group consisting of Na+, K+, Ca++ and Mg++; and n is an integer from 1 to 1000.

2. The compound according to claim 1 wherein $R_2$ is a quaternium group and $R_3$ is a $C_2$ to $C_{22}$ hydrocarbon group.

3. The compound according to claim 1 wherein R', R''', $R_1$, $R_3$, X and Y are each $C_2$ to $C_{22}$ hydrocarbon groups.

4. The compound according to claim 1 wherein R' is a $C_6$ through $C_{36}$ linear, cyclic or branch-chained saturated or unsaturated hydrocarbon group; R'' is a $C_1$ through $C_{36}$ linear, cyclic or branch-chained saturated or unsaturated hydrocarbon group; R''' is a $C_1$ through $C_{36}$ linear, cyclic or branch-chained saturated or unsaturated hydrocarbon group; $R_1$ is a $C_2$ through $C_{22}$ linear or branch-chained saturated or unsaturated unsubstituted hydrocarbon group; $R_2$ is a hydrogen or a quaternium group; $R_3$ is a $C_2$ through $C_{22}$ linear or branch-chained saturated or unsaturated unsubstituted hydrocarbon group; and n is an integer from 2 to 150.

5. The compound according to claim 1 wherein n is an integer from 2 to 150.

6. The compound according to claim 1 wherein R' is an isophorone group.

7. The compound according to claim 2 wherein R' is an isophorone group.

8. The compound according to claim 3 wherein R' is an isophorone group.

9. The compound according to claim 4 wherein R' is an isophorone group.

10. The compound according to claim 5 wherein R' is an isophorone group.

* * * * *